(12) United States Patent
Dusselier et al.

(10) Patent No.: US 11,583,838 B2
(45) Date of Patent: Feb. 21, 2023

(54) ZINCOALUMINOSILICATES WITH GME TOPOLOGIES AND METHODS OF MAKING AND USING THE SAME

(71) Applicant: California Institute Of Technology, Pasadena, CA (US)

(72) Inventors: Michiel J. Dusselier, Kessel-Lo (BE); Mark E. Davis, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 17/377,779

(22) Filed: Jul. 16, 2021

(65) Prior Publication Data

US 2021/0346874 A1 Nov. 11, 2021

Related U.S. Application Data

(62) Division of application No. 15/873,601, filed on Jan. 17, 2018, now Pat. No. 11,167,276, which is a division of application No. 15/050,885, filed on Feb. 23, 2016, now Pat. No. 9,901,909.

(60) Provisional application No. 62/133,074, filed on Mar. 13, 2015, provisional application No. 62/119,945, filed on Feb. 24, 2015.

(51) Int. Cl.
| | |
|---|---|
| *B01J 29/04* | (2006.01) |
| *C01B 39/48* | (2006.01) |
| *B01D 53/86* | (2006.01) |
| *C07C 67/37* | (2006.01) |
| *C07C 29/48* | (2006.01) |
| *C07C 209/14* | (2006.01) |
| *C01B 39/06* | (2006.01) |
| *C07C 29/50* | (2006.01) |
| *C07C 1/20* | (2006.01) |
| *C10G 45/68* | (2006.01) |
| *C10G 3/00* | (2006.01) |
| *C10G 45/64* | (2006.01) |
| *C10G 50/00* | (2006.01) |
| *C10G 49/08* | (2006.01) |
| *C10G 47/20* | (2006.01) |
| *C01B 21/04* | (2006.01) |
| *C07C 7/13* | (2006.01) |
| *B01D 53/94* | (2006.01) |

(52) U.S. Cl.
CPC ........ *B01J 29/048* (2013.01); *B01D 53/8628* (2013.01); *C01B 21/0411* (2013.01); *C01B 39/06* (2013.01); *C01B 39/48* (2013.01); *C07C 1/20* (2013.01); *C07C 7/13* (2013.01); *C07C 29/48* (2013.01); *C07C 29/50* (2013.01); *C07C 67/37* (2013.01); *C07C 209/14* (2013.01); *C10G 3/49* (2013.01); *C10G 45/64* (2013.01); *C10G 45/68* (2013.01); *C10G 47/20* (2013.01); *C10G 49/08* (2013.01); *C10G 50/00* (2013.01); *B01D 53/9418* (2013.01); *B01D 2251/2062* (2013.01); *B01D 2255/20792* (2013.01); *B01D 2255/50* (2013.01); *B01J 2229/186* (2013.01); *C07C 2521/12* (2013.01); *C07C 2523/06* (2013.01); *C07C 2529/70* (2013.01); *C10G 2300/1088* (2013.01); *C10G 2300/1096* (2013.01); *C10G 2400/22* (2013.01); *C10G 2400/30* (2013.01); *Y02C 20/10* (2013.01); *Y02C 20/30* (2013.01); *Y02P 20/52* (2015.11); *Y02P 30/20* (2015.11); *Y02P 30/40* (2015.11)

(58) Field of Classification Search
None
See application file for complete search history.

(56) References Cited

U.S. PATENT DOCUMENTS

| | | |
|---|---|---|
| 3,140,249 A | 7/1964 | Plank et al. |
| 3,140,251 A | 7/1964 | Plank et al. |
| 3,140,253 A | 7/1964 | Plank et al. |
| 3,904,738 A | 9/1975 | Robson |
| 4,061,717 A | 12/1977 | Kerr et al. |
| 4,503,024 A | 3/1985 | Bourgogne et al. |
| 4,544,538 A | 10/1985 | Zones |
| 5,283,047 A | 2/1994 | Vaughan et al. |
| 5,958,370 A | 9/1999 | Zones et al. |
| 6,086,848 A | 7/2000 | Nakagawa et al. |
| 6,187,283 B1 | 2/2001 | Chiyoda et al. |
| 6,423,295 B1 | 7/2002 | Huo |
| 7,008,610 B2 | 3/2006 | Cao et al. |
| 9,364,782 B1 | 6/2016 | Xie et al. |
| 10,399,858 B2 | 9/2019 | Dusselier et al. |
| 2002/0076376 A1 | 6/2002 | Huo |
| 2002/0119887 A1 | 8/2002 | Huo et al. |
| 2005/0154244 A1 | 7/2005 | Cao et al. |

(Continued)

FOREIGN PATENT DOCUMENTS

| | | |
|---|---|---|
| EP | 1216960 A2 | 6/2002 |
| WO | 99/08961 A1 | 2/1999 |

(Continued)

OTHER PUBLICATIONS

Bleken, et al., "The Effect of Acid Strength on the Conversion of Methanol to Olefins Over Acidic Microporous Catalysts with the CHA Topology", Top. Catal. Jan. 2009, vol. 52, 218-228.

(Continued)

*Primary Examiner* — Yun Qian
(74) *Attorney, Agent, or Firm* — BakerHostetler

(57) ABSTRACT

The present disclosure is directed to methods of producing zincoaluminosilicate structures with AEI, CHA, and GME topologies using organic structure directing agents (OSDAs), and the compositions and structures resulting from these methods.

27 Claims, 7 Drawing Sheets

(56) References Cited

U.S. PATENT DOCUMENTS

2005/0197519 A1  9/2005  Cao et al.

FOREIGN PATENT DOCUMENTS

| | | |
|---|---|---|
| WO | 2005/063624 A1 | 7/2005 |
| WO | 2008/016423 A1 | 2/2008 |

OTHER PUBLICATIONS

Burton, et al., "Organic Molecules in Zeolite Synthesis: Their Preparation and Structure Directing Effects", In Stud. Surf. Sci. Catal., Elsevier: 2007; vol. 168, 37-179.
Cartlidge, et al. "Hydrothermally Stable Chabazites for the Selective Preparation of Olefins from Methanol", In Zeolites: Facts, Figures, Future, Jacobs, Eds. Elsevier: Amsterdam, 1989, 1151-1161.
Chen et al., "IR Spectroscopic Study of CD3CN Adsorbed on ALPO-18 Molecular Sieve and the Solid Acid Catalysts SAPO-18 and MeAPO-18", J. Chem. Soc., Jan. 1994, 90(22), 3455-3459.
Chen et al., "SAPO-18 Catalysts and Their Bronsted Acid Sites", J. Phys. Chem., Sep. 1994, 98, 10216-10224.
Chen, et al., "MAPO-18 (M=Mg, Zn, Co): A New Family of Catalysts for the Conversion of Methanol to Light Olefins", Chem. Soc., Chem. Commun., Jan. 1994, 603-604.
Chiyoda et al., "Hydrothermal Conversion of Y-Zeolite Using Alkaline-Earth Cations", Micro. and Meso. Mat., 1999, 32, 257-264.
Chiyoda, et al., "Adsorption Studies with Gmelinite Zeolites Containing mono-di and tri-valent Cations", Micro. and Meso. Mat., 2000, 38, 143-149.
Daniels et al., "Cationic Polymers a Templates in Zeolite Crystallization", Amer. Chemical Society, May 10, 1978, 3097-3100.
Davis et al., "Synthesis of Gmelinite and ZSM-12 Zeolites with a Polymer Template", J. Chem. Soc., 1988, 920-921.
Davis, et al., "Zeolite and Molecular Sieve Synthesis", Chem. Mater., 1992, vol. vol. 4, 756-768.
Dusselier et al., "Influence of Organic Structure Directing Agent Isomer Distribution on the Synthesis of SSZ-39," Chemistry of Materials, Mar. 30, 2015, vol. 27, 2695-2702.
Froment, et al., In Catalysis in the Conversion of Methanol into Olefin, Spivey, J. J., Ed. The Royal Society of Chemistry, 1992, vol. 9(1), 64 pgs.
Hunsicker et al., "Framework Zinc-Substituted Zeolites: Synthesis, and Core-Level and Valence-Band XPS", Chem. Mater., Oct. 8, 2002, 14, 4807-4811.
Ji, et al., "Organic-Free Synthesis of CHA-Type Zeolite Catalysts for the Methanol-to-Olefins Reaction", ACS Catalysis, 2015, vol. 5, 4456-4465.
Martin, et al., "Efficient Synthesis of the Cu-SSZ-39 Catalyst for DeNOx Applications (Electronic Supplementary Information)" Royal Society of Chemistry Journal, 2015, 10 pgs.
Martin, et al., "Efficient Synthesis of the Cu-SSZ-39 Catalyst for DeNOxApplications", Royal Society of Chemistry Journal, Jan. 2012, 4 pgs.
Moliner, et al., "Cu-SSZ-39, an Active and Hydrothermally Stable Catalyst for the Selective Catalytic Reduction of NOx", Chem. Commun., 2012, 48(66), 8264-8266.
Olsbye, et al., "Conversion of Methanol to Hydrocarbons: How Zeolite Cavity and Pore Size Controls Product Selectivity", Angew. Chem. Int. Ed., Apr. 2012, vol. 51(24), 5810-5831.
Ren, et al., Designed Copper-Amine Complex as an Efficient Template for One-Pot Synthesis of Cu-SSZ-13 Zeolite with Excellent Activity for Selective Catalytic Reduction of NOxbY NH/, Chem Commun., May 2011, 47, 9789-9791.
Tsuda et al., "Catalytic Hydrogenation of Dimethylpyridine Methiodides and Stereochemistry of Hydrogenation Products," Chemical and Pharmaceutical Bulletin, 1970, vol. 18(12), 2499-2506.
Tsuiji, et al., "Synthesis of 4,4'-trimethylenebis(1-benzyl-1-methylpiperidinium) diastereomers and their use as structure-directing agents in pure-silica molecular sieve syntheses", Microporous and Mesoporous Materials, 28(3), May 1999, 519-530.
Vermeiren, et al., "Impact of Zeolites on the Petroleum and Petrochemical Industry", Top. Catal. 2009, 52(9), 1131-1161.
Wagner, et al., "Guest/Host Relationships in the Synthesis of the Novel Cage-Based Zeolites SSZ-35, SSZ-36, and SSZ-39", J. Am. Chem. Soc., Dec. 1999, 122, 263-273.
Wang, et al., "Dealumination of Zeolites—II. Kinetic Study of the Dealumination by Hydrothermal Treatment of a NH4NaY Zeolite", J. Catal., Aug. 1991, vol. 130(2), 459-470.
Wu et al., "Mesoporous SSZ-13 Zeolite Prepared by a Dual-Template Method with Improved Performance in the Methanol-to-Olefins Reaction", J. Catal., Feb. 2013, vol. 298, 27-40.
Yuen, et al., "Product Selectivity in Methanol to Hydrocarbon Conversion for Isostructural Compositions of AFI and CHA Molecular Sieves", Microporous Mater., Feb. 1994, 2(2), 105-117.
Zones et al., "Searching for New High Silica Zeolites Through a Synergy of Organic Templates and Novel Inorganic Conditions", Micro and Meso Mat., 1998, 199-211.
U.S. Appl. No. 15/873,601, filed Jan. 17, 2018.
U.S. Appl. No. 15/050,885, filed Feb. 23, 2016.

ZINCOALUMINOSILICATES WITH GME TOPOLOGIES AND METHODS OF MAKING AND USING THE SAME

CROSS REFERENCE TO RELATED APPLICATIONS

This application is a divisional of U.S. patent application Ser. No. 15/873,601, filed Jan. 17, 2018, which is a divisional of U.S. patent application Ser. No. 15/050,885, filed Feb. 23, 2016, now U.S. Pat. No. 9,901,909 that issued Feb. 27, 2018, which claims priority to U.S. patent application Ser. No. 62/119,945 filed Feb. 24, 2015 and U.S. Patent Application Ser. No. 62/133,074 filed Mar. 13, 2015, the contents of which are incorporated by reference herein in their entireties for all purposes.

TECHNICAL FIELD

The present disclosure is directed to methods of producing zincoaluminosilicate structures with GME topologies using organic structure directing agents (OSDAs), and the compositions and structures resulting from these methods.

BACKGROUND

The aluminosilicate version of the molecular sieve with the framework topology code AEI was first reported in 1997 and it was given the name SSZ-39. The previous materials with the AEI framework features were AlPO-18 (an aluminophosphate) and SAPO-18 (a silicoaluminophosphates). The AEI framework describes a material that has 8-membered ring (MR) openings and constitutes a 3D channel (8×8×8) system with equal pore sizes of 3.8×3.8 Å and medium size cages that can contain spheres up to 7.3 Å. Lately, there has been an increase of interest in 8MR systems for catalysis and gas separations. Two very promising catalytic applications are the methanol (or oxygenates) to olefins conversion (MTO) and the selective catalytic reduction (SCR) of $NO_x$ in flue and exhaust gases. Specific 8MR materials of interest for such applications have been found within the CHA, LEV, AFX, KFI, RTH and AEI topologies. More specifically, Cu-exchanged AEI type materials, such as Cu-SAPO-18 and Cu-SSZ-39, have been found to be very efficient and stable in the SCR reaction.

SAPO materials and zeolites only provide exchange sites for divalent ions (such as $Cu^{2+}$) when framework heteroatom (Al in the zeolite case, Si in the SAPO case) substitution is high and these sites are close to each other. This can for instance occur in bridged substitution sites, as seen in FIG. 1(A) for zeolites or when the sites are close enough due to the shape of the composite building unit of the framework, as seen in FIG. 1(B) for a d6r zeolite building block. A molecular sieve with divalent species built in into a siliceous framework in a tetrahedral fashion ideally gives the framework a local charge deficit of −2. This local charge deficit can be balanced by cationic species such as $H^+$, $Na^+$, $Li^+$, et cetera but also by divalent cations such as $Cu^{2+}$, $Ca^{2+}$, $Ni^{2+}$, etc. as shown in FIG. 1(C) for zincosilicates. The catalytic and gas separation properties of molecular sieves highly depend on the type of exchanged cations and the framework sites they balance. For the SCR of $NO_x$ with zeolites, it has been noted that only divalent cationic $Cu^{2+}$, ideally exchanged near two negative framework charges, are key in the catalytic cycle. Over-exchanged samples, for instance when $[Cu(OH)]^+$ species are present near a negative framework charge, could be less appealing. In most aluminosilicate materials, the amount of divalent exchange sites are thus limited and require the use of zeolites with a low Si/Al ratio. The introduction of Zn along with Al in suited zeolites, creating zincoaluminosilicates, would therefore increase the number of (divalent) exchange sites. Moreover, active sites for sorption and catalysis derived from cations exchanged on framework Zn, or the framework Zn site itself, could react differently compared to classic Al-based active sites.

However, the use of zincosilicate molecular sieves can often be limited due to their lower stability against hydrolysis or collapse, which is especially striking compared to the high stability of silicate or aluminosilicate molecular sieves. Therefore, and for other reasons of catalytic nature, it is desirable to create zincoaluminosilicate materials, rather than pure zincosilicates. Synthesizing such materials is difficult and only very few have ever been reported. A notable example is a VET analogue called SSZ-41 which can contain both Zn and Al in the framework. However, this material closely resembles the VPI-8 material, which is a pure zincosilicate, due to its very low aluminum content. Other documented zincoaluminosilicates are found in MAZ, OFF, and FAU topologies but there, the proof of Zn incorporation is not unambiguous. Materials incorporating both Zn and Al in appropriate amounts are hard to make, especially since the presence of Zn in synthesis gels is known to either favor formation of (or direct to) only a couple of frameworks (such as ANA and VET) or inhibit zeolite formation entirely.

The present invention is directed to addressing at least some of the shortcomings of the existing art.

SUMMARY

The present invention is directed to the use of quarternary salts under certain conditions to prepare zincoaluminosilicates with AEI, CHA, and GME topologies, and the novel materials derived from these processes. This disclosure presents a new synthetic approach towards zincoaluminosilicates and materials and process applications derived from that approach.

Certain embodiments of the present invention include those processes comprising preparing a zincoaluminosilicate composition of an AEI or GME topology, each process comprising hydrothermally treating an aqueous composition comprising:

(a) a source of a silicon oxide, and optionally a source of germanium oxide or combination thereof;

(b) a source of aluminum oxide, and optionally a source of boron oxide, gallium oxide, hafnium oxide, iron oxide, tin oxide, titanium oxide, indium oxide, vanadium oxide, zirconium oxide, or combination or mixture thereof; and (c) a source of a zinc oxide;

(d) a mineralizing agent; and (e) an organic structure directing agent (OSDA) comprising at least one isomer of the quaternary piperidinium cation of Formula (I):

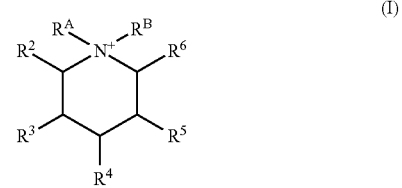

under conditions effective to crystallize a crystalline microporous zincoaluminosilicate solid of AEI or GME topology; wherein $R^A$ and $R^B$ are independently a $C_{1-3}$ alkyl, or together with the N to which they are bound form a 5 or 6 membered saturated or unsaturated ring; and $R^2$, $R^3$, $R^4$, $R^5$, and $R^6$ are independently H or $C_{1-3}$ alkyl, provided at least two of $R^2$, $R^3$, $R^4$, $R^5$, and $R^6$ are independently $C_{1-3}$ alkyl.

The quaternary piperidinium cation of Formula (I) is defined in various embodiments in terms of sub-genera and specific quaternary piperidinium cations. For example, in some embodiments, the quaternary piperidinium cation is defined in terms of:

(a) structures of Formula (IA) or (IB):

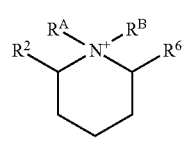

(IA)

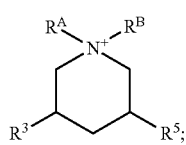

(IB)

(b) certain N,N-dialkyl-2,6-lupetidinium cation or an N,N-dialkyl-3,5-lupetidinium cation:

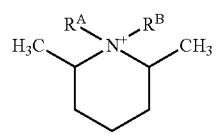 or 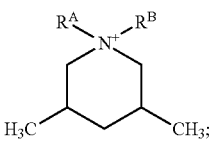

(c) cis-N,N-dialkyl-3,5-lupetidinium cation, trans-N,N-dialkyl-3,5-lupetidinium cation, cis-N,N-dialkyl-2,6-lupetidinium cation, trans-N,N-dialkyl-2,6-lupetidinium cation or a combination thereof, and (d) cis-N,N-dimethyl-3,5-lupetidinium cation, trans-N,N-dimethyl-3,5-lupetidinium cation, cis-N,N-dimethyl-2,6-lupetidinium cation, trans-N,N-dimethyl-2,6-lupetidinium cation or a combination thereof.

In general, the quaternary 3,5 piperidinium cations, or mixtures comprising these cations are preferred, particularly, cis-N,N-dialkyl-3,5-lupetidinium cation, or cis-N,N-dimethyl-3,5-lupetidinium cation, of mixtures comprising these cations.

Other embodiments include those processes comprising preparing a zincoaluminosilicate composition of CHA topology, each process comprising hydrothermally treating an aqueous composition comprising:

(a) a source of a silicon oxide, and optionally a source of germanium oxide or combination thereof;

(b) a source of aluminum oxide, and optionally a source of boron oxide, gallium oxide, hafnium oxide, iron oxide, tin oxide, titanium oxide, indium oxide, vanadium oxide, zirconium oxide, or combination or mixture thereof, and (c) a source of a zinc oxide;

(d) a mineralizing agent; and (e) an organic structure directing agent (OSDA) comprising a trialkyladamantylammonium cation of Formula (II) or an optionally substituted trialkylbenzylammonium cation of Formula (III):

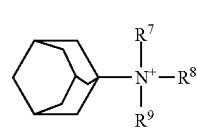

(II)

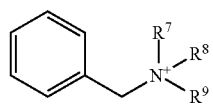

(III)

under conditions effective to crystallize a crystalline microporous zincoaluminosilicate solid of CHA topology; wherein:

$R^7$, $R^8$, and $R^9$ are independently $C_{1-6}$ alkyl or $C_{1-3}$ alkyl; and wherein the quaternary trialkyladamantyl- or trialkylbenzyl-ammonium cation has an associated bromide, chloride, fluoride, iodide, or hydroxide anion.

The trialkyladamantylammonium cation of Formula (II) and substituted trialkylbenzylammonium cation of Formula (III) are also described in certain subgenera and specific compounds.

The nature of the sources of the various oxides and their ratio ranges, the nature of the mineralizing agent, and the hydrothermal heating conditions are also disclosed as separate embodiments.

The products of the hydrothermal treating may be isolated and subjects to one or more of further processing conditions, in some cases specific to the nature of the isolated solid's topology. Such treatments include:

(a) heating the isolated crystalline microporous zincoaluminosilicate solids at a temperature in a range of from about 250° C. to about 600° C.;

(b) contacting the isolated crystalline microporous zincoaluminosilicate solid with ozone or other oxidizing agent at a temperature in a range of 100° C. to 200° C.; and (c) heating the isolated crystalline microporous zincoaluminosilicate solid at a temperature in a range of from about 200° C. to about 600° C. in either the absence or the presence of an alkali, alkaline earth, transition metal, rare earth metal, ammonium or alkylammonium salts;

in each case for a time sufficient to form a dehydrated or an OSDA-depleted crystalline microporous zincoaluminosilicate product. Certain subembodiments describe specific aspects of these treatments.

These dehydrated or OSDA-depleted crystalline microporous zincoaluminosilicate products may be further treated with an aqueous ammonium or metal cation salt and/or with at least one type of transition metal or transition metal oxide.

Various embodiments disclose the compositions prepared by any one of the processes embodiments. These include compositions which may be described as:

(a) compositions comprising the aqueous compositions used in the hydrothermal treatments together with a compositionally consistent crystalline microporous zincoaluminosilicate product, the compositionally consistent crystalline microporous zincoaluminosilicate products containing the respective OSDAs used in their preparation occluded in their pores;

(b) the isolated crystalline microporous zincoaluminosilicate products which contain the respective OSDAs used in their preparation occluded in their pores; and (c) the crystalline microporous zincoaluminosilicate products from which the OSDAs have been dehydrated or substantially depleted from their pores and/or which have been post-treated to add salts, metals, or metal oxides into the pores of the crystalline microporous zincoaluminosilicate products.

While these compositions have been described and claimed in terms of the processes used to prepare them, other embodiments describe and claim these compositions in terms which do not require these process limitations. For example, certain embodiments disclose compositions of crystalline microporous zincoaluminosilicate solids of AEI, CHA, or GME topologies. In other embodiments, the zincoaluminosilicate solids are described in terms of the ratios of the respective components. For example, in certain embodiments, the zincoaluminosilicate solids of AEI or GME topologies, whether containing the OSDA or not, have molar ratio of Si:Al in a range of from 3 to about 200 (or $SiO_2/Al_2O_3$ ratio of from 6 to 400) and molar ratios of Si:Zn in a range from 5 to 50. In other embodiments, the zincoaluminosilicate solid of CHA topologies have molar ratio of Si:Al in a range of from 4 to 100 (or $SiO_2/Al_2O_3$ ratio from 8 to 200) and a molar ratios of Si:Zn in a range from 5 to 50. Independent embodiments provide subsets of these ranges.

In other embodiments, the zincoaluminosilicate solids are described in terms of certain physical characteristics of the zincoaluminosilicate solids, for example with respect to XRD patterns, $^{29}$Si MAS NMR spectra, and thermogravimetric analysis (TGA) data.

Other embodiments include the processes directed to a range of organic transformations catalyzed by catalysts comprising the crystalline microporous zincoaluminosilicates. Among these processes are those directed to reducing NOx in exhaust gases by catalytic reduction, converting methane via partial oxidation to methanol, and converting lower alcohols and other oxygenates to at least one type of olefin.

These inventive zincoaluminosilicates are also useful as ion exchange media, and various embodiments consider such applications

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods of making and methods of using, processes, devices, and systems disclosed. In addition, the drawings are not necessarily drawn to scale. In the drawings.

DETAILED DESCRIPTION OF ILLUSTRATIVE EMBODIMENTS

Figure 1A:
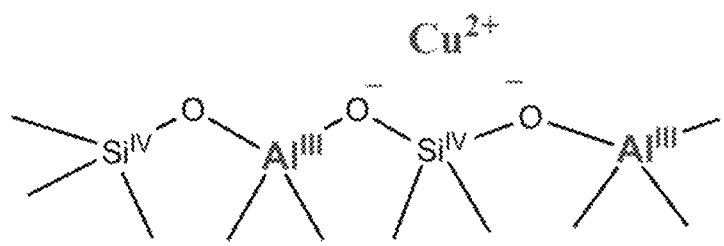
FIGS. 1(A)-(C) show some of the different molecular sieve exchange sites created by Al substitution in zeolites (FIG. 1(A), bridged Al substitutions, and FIG. 1(B), Al-substitutions close to each other in the d6r building block—oxygen atoms omitted for clarity) and Zn substitution in zincosilicates (FIG. 1(C)).

The present invention is directed to methods preparing microporous crystalline zincoaluminosilicate compositions of AEI, CHA, and GME topologies using piperidinium based Organic Structure Directing Agents (OSDAs), and the compositions derived from these methods.

This disclosure describes the synthesis and properties of a novel molecular sieve containing both Zn and Al as heteroatoms in the zeolite's framework (zincoaluminosilicates) The new material is crystalline and isostructural with AlPO-18 and SSZ-39, as it has a framework with the AEI topology (framework code of the structure commission of the International Zeolite Association). The synthesis of zincoaluminosilicates with the GME and CHA topologies are also shown.

The present invention may be understood more readily by reference to the following description taken in connection with the accompanying Figures and Examples, all of which form a part of this disclosure. It is to be understood that this invention is not limited to the specific products, methods, processes, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this specification, claims, and drawings, it is recognized that the descriptions refer to compositions and processes of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

Terms

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method or process steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of" For those embodiments provided in terms of "consisting essentially of," the basic and novel characteristic(s) of a process is the ability to provide the named zincoaluminosilicate using the named OSDAs without additional components, even if such components are present.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

Unless otherwise stated, ratios or percentages are intended to refer to mole percent or atom percent, as appropriate.

Throughout this specification, words are to be afforded their normal meaning, as would be understood by those skilled in the relevant art. However, so as to avoid misunderstanding, the meanings of certain terms will be specifically defined or clarified.

"Lower alcohols" or lower alkanes refer to alcohols or alkanes, respectively, having 1-10 carbons, linear or branched, preferably 1-6 carbon atoms and preferably linear. Methanol, ethanol, propanol, butanol, pentanol, and hexanol are examples of lower alcohols. Methane, ethane, propane, butane, pentane, and hexane are examples of lower alkanes.

The terms "oxygenated hydrocarbons" or "oxygenates" as known in the art of hydrocarbon processing to refer to components which include alcohols, aldehydes, carboxylic acids, ethers, and/or ketones which are known to be present in hydrocarbon streams or derived from biomass streams other sources (e.g. ethanol from fermenting sugar).

The terms "separating" or "separated" carry their ordinary meaning as would be understood by the skilled artisan, insofar as they connote physically partitioning or isolating the product material from other starting materials or co-products or side-products (impurities) associated with the reaction conditions yielding the material. As such, it infers that the skilled artisan at least recognizes the existence of the product and takes specific action to separate or isolate it from starting materials and/or side- or byproducts. Absolute purity is not required, though it is preferred.

Unless otherwise indicated, the term "isolated" means physically separated from the other components so as to be free of at least solvents or other impurities, such as starting materials, co-products, or byproducts. In some embodiments, the isolated crystalline materials, for example, may be considered isolated when separated from the reaction mixture giving rise to their preparation, from mixed phase co-products, or both. In some of these embodiments, for example, pure zincoaluminosilicates (or structures containing incorporated OSDAs) can be made directly from the described methods. In some cases, it may not be possible to separate crystalline phases from one another, in which case, the term "isolated" can refer to separation from their source compositions.

"Optional" or "optionally" means that the subsequently described circumstance may or may not occur, so that the description includes embodiments where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present. Similarly, the phrase "optionally isolated" means that the target material may or may not be separated from other materials used or generated in the method, and, thus, the description includes separate embodiments where the target molecule or other material is separated and where the target material is not separated, such that subsequence steps are conducted on isolated or in situ generated product.

The terms "method(s)" and "process(es)" are considered interchangeable within this disclosure.

As used herein, the term "crystalline microporous solids" or "crystalline microporous silicate or aluminosilicate solids," sometimes referred to as "molecular sieves," are crystalline structures having very regular pore structures of molecular dimensions, i.e., under 2 nm. The term "molecular sieve" refers to the ability of the material to selectively sort molecules based primarily on a size exclusion process. The maximum size of the species that can enter the pores of a crystalline microporous solid is controlled by the dimensions of the channels. These are conventionally defined by the ring size of the aperture, where, for example, the term "8-MR" or "8-membered ring" refers to a closed loop that is typically built from eight tetrahedrally coordinated silicon (or aluminum) atoms and 8 oxygen atoms. These rings are not necessarily symmetrical, due to a variety of effects including strain induced by the bonding between units that are needed to produce the overall structure, or coordination of some of the oxygen atoms of the rings to cations within the structure. The term "silicate" refers to any composition including silicate (or silicon oxide) within its framework. It is a general term encompassing, for example, pure-silica (i.e., absent other detectable metal oxides within the framework), aluminosilicate, borosilicate, or titanosilicate structures. The term "zeolite" refers to an aluminosilicate composition that is a member of this family. The term "aluminosilicate" refers to any composition including silicon and aluminum oxides within its framework. In some cases, either of these oxides may be substituted with other oxides. "Pure aluminosilicates" are those structures having no detectable other metal oxides in the framework. As long as the framework contains silicon and aluminum oxides, these substituted derivatives fall under the umbrella of aluminosilicates. Similarly, the term "zincoaluminosilicate" refers to any composition including silicon, aluminum, and zinc oxides within its framework. Such zincoaluminosilicates may be "pure-zincoaluminosilicates (i.e., absent other detectable metal oxides within the framework) or optionally substituted. When described as "optionally substituted," the respective framework may contain boron, gallium, hafnium, iron, tin, titanium, indium, vanadium, zirconium, or other atoms substituted for one or more of the aluminum, silicon, or zinc atoms not already present in in the framework.

The present disclosure describes and is intended to lay claim to methods of making crystalline compositions, the compositions themselves, and methods of using the crystalline zincoaluminosilicate compositions having an AEI, CHA, or GME framework. The structural features associated with the AEI, CHA, and GME topologies are well-understood by those skilled in the art and are summarized, for example, in the Database of Zeolite Structures, maintained by the International Zeolite Association (IZA-SC). The most recently available Database at the timing of this disclosure is incorporated by reference for its descriptions of these topologies. Also as described elsewhere as well, it should be appreciated that any embodied feature described for one of these categories (i.e., compositions and methods of making or using) is applicable to all other categories.

Processes of Preparing Crystalline Compositions

Certain embodiments of the present invention include those processes for preparing and using crystalline zincoaluminosilicate compositions having an AEI, CHA, or GME framework. These include hydrothermally treating specific compositions to prepare certain compositions, isolating the resulting crystalline materials, further post-processing of these isolated materials, and a range of catalytic reactions which use them. Other embodiments include the compositions derived from these preparatory processes. The disclosure also provide characterizations of a range of associated compositions, which are independent of the means of making them. While many of the aspects of the processes for preparing the AEI-, CHA-, and GME-type share common features, as to the processes using them, there are distinctions. For the sake of clarity, these distinctions will be discussed separately.

AEI and GME Topologies

Certain embodiments involve those process for preparing a zincoaluminosilicate composition having an AEI or GME topology, each process comprising hydrothermally treating an aqueous composition comprising:

(a) a source of a silicon oxide, and optionally a source of germanium oxide or combination thereof;

(b) a source of aluminum oxide, and optionally a source of boron oxide, gallium oxide, hafnium oxide, iron oxide, tin oxide, titanium oxide, indium oxide, vanadium oxide, zirconium oxide, or combination or mixture thereof; and (c) a source of a zinc oxide;

(d) a mineralizing agent; and (e) an organic structure directing agent (OSDA) comprising at least one isomer of the quaternary piperidinium cation of Formula (I):

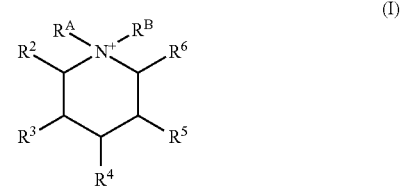

under conditions effective to crystallize a crystalline microporous zincoaluminosilicate solid of AEI or GME topology; wherein $R^A$ and $R^B$ are independently a $C_{1-3}$ alkyl, or together with the N to which they are bound form a 5 or 6 membered saturated or unsaturated ring; and $R^2$, $R^3$, $R^4$, $R^5$, and $R^6$ are independently H or $C_{1-3}$ alkyl, provided at least two of $R^2$, $R^3$, $R^4$, $R^5$, and $R^6$ are independently $C_{1-3}$ alkyl.

The counterion to the cationic organic structure directing agent mixture in Formula (I) (and in Formulae (II) and (III) discussed elsewhere) is generally a bromide, chloride, fluoride, iodide, or hydroxide ion, but the OSDA may be added also to the composition as an acetate, nitrate, or sulfate. In some embodiments, the quaternary piperidinium cation has an associated fluoride or hydroxide ion preferably substantially free of other halide counterions. In separate embodiments, the associated anion is hydroxide.

It should be appreciated that the instant invention provides that the quaternary piperidinium cation may comprise one or more stereoisomers of the same structural compound or two or more different compounds, selected from these options. For the sake of brevity, reference to an isomer by individual digits is intended to refer to that isomer substituted in that position. For example, the "2,6 isomer" refers to an isomer containing an alkyl substituent only in the $R^2$ and $R^6$ positions; a "3,5 isomer" refers to an isomer containing an alkyl substituent only in the $R^3$ and $R^5$ positions.

Reference to "isomers" in Formula (I) (and Formula (IA) and (IB) discussed elsewhere) refers to both structural and stereochemical isomers of the quaternary piperidinium cation. That is, reference to two or more isomers may encompass multiple structural isomers (e.g., individual mono-alkyl compounds substituted in the 2, 3, 4, 5, or 6 positions, or di-alkyl compounds substituted in the 2,3 and 2,4 and 2,5 and 2,6, and 3,4 and 3,5, and 4,5 positions, or combinations thereof). In some cases, these may include mixtures of homologs (e.g., where $R^2$ is methyl and $R^6$ is ethyl), stereoisomers of the same structural isomer (e.g., cis-2-methyl/6-methyl and trans-2-methyl/6-methyl), or combinations of both (e.g., cis-2-methyl/6-methyl and trans-2-methyl/6-ethyl).

For example, referring to the structure of Formula (I), options for the quaternary piperidinium cations include those where $R^2$, $R^3$, $R^4$, $R^5$, and $R^6$ are individually and independently methyl, ethyl, n-propyl, or iso-propyl, independent of stereochemistry. In separate embodiments, the carbon skeleton of piperidinium cation may be di-, tri-, tetra-, or penta-substituted with any of these $C_{1-3}$ alkyl groups, independent of stereochemistry.

The piperidine frameworks which derive the quaternary piperidinium cations may be conveniently derived from the hydrogenation of di-, tri, or tetraalkyl pyridine, via the intermediary formation of the corresponding di-, tri, or tetraalkyl piperidinium precursors, for example using $Pt/H_2$ or Raney Nickel catalysts. Given the availability of such pyridine precursors, in some embodiments, dialkyl piperidinium frameworks are conveniently obtained by such processes, especially, for example, where $R^3$ and $R^5$ are alkyl, preferably ethyl or methyl, more preferably methyl or where $R^2$ and $R^6$ are alkyl, preferably ethyl or methyl, more preferably methyl. In the former case, where $R^3$ and $R^5$ are methyl and $R^2$, $R^4$, and $R^6$ are H, the structures are known as 3,5-lupetidinium cations. In the latter case, where $R^2$ and $R^6$ are methyl and $R^3$, $R^4$, and $R^5$ are H, the structures are known as 2,6-lupetidinium cations.

$R^A$ and $R^B$ are defined as being independently a $C_{1-3}$ alkyl, or together with the N to which they are bound form a 5 or 6 membered saturated or unsaturated ring. As such, in some embodiments, $R^A$ and $R^B$ are independently methyl, ethyl, n-propyl, or iso-propyl. In other embodiments, $R^A$ and $R^B$, together with the N to which they are bound, form a 5 or 6 membered saturated or unsaturated ring. For example, these may include structures described as a spiro-pyrrolidinium moiety, also described as a 5-azonia-spiro [4,5] decane:

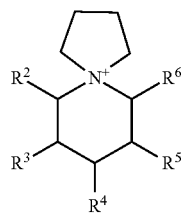

or a spiro-piperidinium moiety, also described as a 6-azonia-spiro [4,5] undecane:

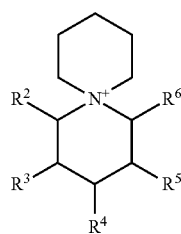

or a spiro-2,5-dihydro-1H-pyrrolium moiety, also described as a 5-azonia-spiro [4,5] dec-2-ene:

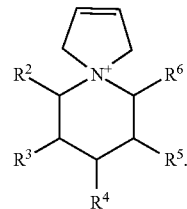

Again, in certain embodiments of these structures, the 2,6 positions (i.e., $R^2$ and $R^6$) are alkyl, preferably ethyl or methyl, more preferably methyl, the remaining positions being H. In other embodiments, the 3,5 positions (i.e., $R^3$ and $R^5$) are alkyl, preferably ethyl or methyl, more preferably methyl, the remaining positions being H.

The use of isomeric mixtures of these quaternary piperidinium cations to prepare aluminosilicate (but not zincoaluminosilicate) frameworks of AEI topology, and their use at catalysts in certain organic transformation have recently been disclosed by the present inventors. See U.S. patent application Ser. No. 14/929,571, filed Jan. 26, 2016, which is incorporated by reference herein in its entirety for all purposes.

In some embodiments, the OSDA used in these processes comprises at least one isomer of the quaternary piperidinium cation of Formula (IA) or (IB):

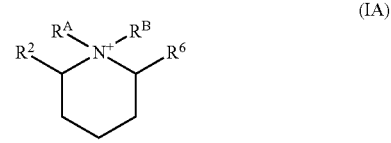

(IA)

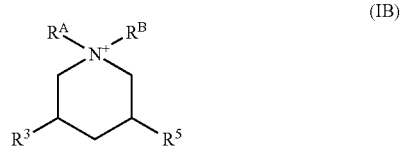

(IB)

wherein $R^2$ $R^3$, $R^5$, and $R^6$ are independently $C_{1-3}$ alkyl.

In some embodiments, the quaternary piperidinium cation of Formula (I) is or comprises an N,N-dialkyl-2,6-lupetidinium cation or an N,N-dialkyl-3,5-lupetidinium cation:

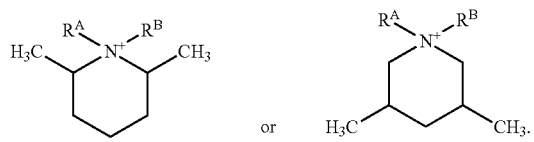

where $R^A$ and $R^B$ are $C_{1-3}$ alkyl, preferable methyl. In separate independent embodiments, the quaternary piperidinium cation of Formula (I) is or comprises an N,N-dialkyl-2,6-lupetidinium cation or an N,N-dialkyl-3,5-lupetidinium cation.

In related embodiments, the quaternary piperidinium cation of Formula (I) is an N,N-dimethyl-3,5-lupetidinium cation, N,N-dimethyl-2,6-lupetidinium cation, N,N-diethyl-3,5-lupetidinium cation, N,N-diethyl-2,6-lupetidinium cation, a 6,10-dimethyl-5-azonia-spiro[4.5]decane, a 1,5-dimethyl-6-azonia-spiro[5.5]undecane, a 7,9-dimethyl-5-azonia-spiro[4.5]decane, a 2,4-dimethyl-6-azonia-spiro[5.5]undecane, or a combination thereof.

5-lupetidinium cation and trans-N,N-dimethyl-3,5-lupetidinium cation, a mixture of cis-N,N-dimethyl-3,5-lupetidinium cation and trans-N,N-dimethyl-3,5-lupetidinium cation, or a combination thereof.

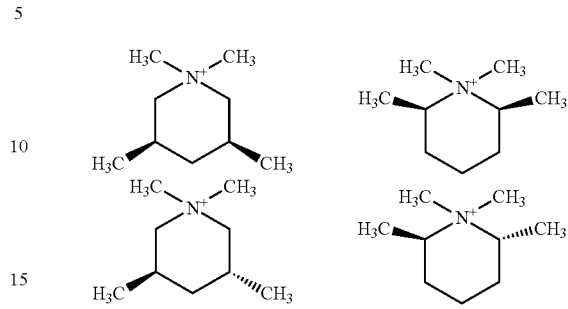

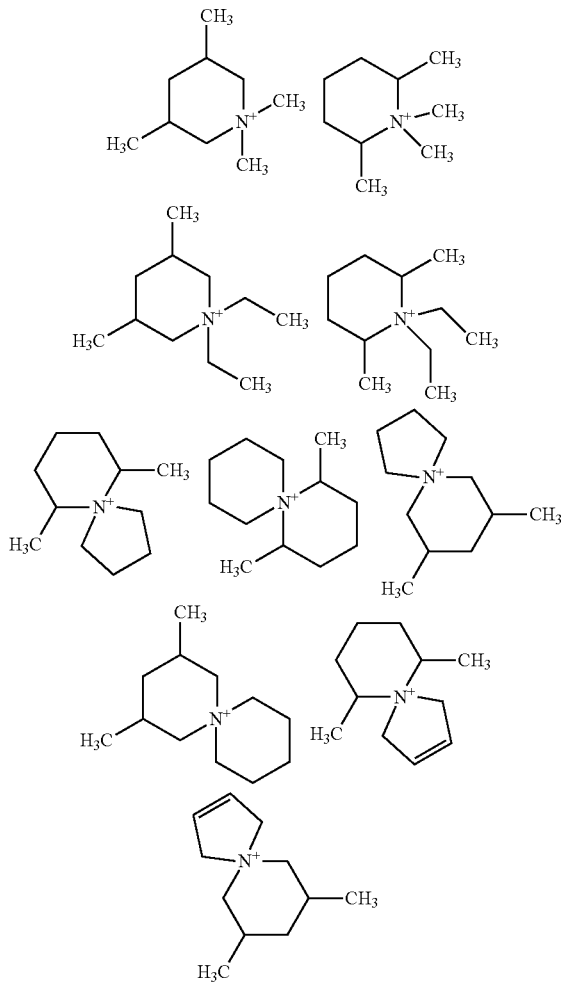

In some embodiments, the ratios of cis and trans in these di-substituted materials may range from about 95% cis/5% trans to about 0% cis/100% trans. In other embodiments, the at least two isomers of the quaternary piperidinium cation of Formula (I) comprise a mixture of cis-N,N-dimethyl-3,5-lupetidinium cation and trans-N,N-dimethyl-3,5-lupetidinium cation in a mole ratio of about 99% cis/1% trans to about 0% cis/100% trans. Other embodiments provide that these ratios range from about 98:2 to 95:5, from about 95:5 to 90:10, from 90:10 to 80:20, from 80:20 to 70:30, from 70:30 to 60:40, from 60:40 to 50:50, 50:50 to 40:60, from 40:60 to 30:70, from 30:70 to 20:80, from 20:80 to 10:90, from 10:90 to 0:100, from 95:5 to 75:25, from 75:25 to 50:50, from 50:50 to 25:75, from 25:75 to 5:100, or any combination of two or more of these ranges, including overlapping ranges, for example from 90:10 to 75:25. In each case, the ratios are mole % cis/mol % trans. As described elsewhere, cis-N,N-dimethyl-3,5-lupetidinium cations, or mixtures containing predominantly cis-N,N-dimethyl-3,5-lupetidinium cations are preferred.

CHA Topologies

Certain other embodiments involve those process for preparing a zincoaluminosilicate composition having a CHA topology, each process comprising hydrothermally treating an aqueous composition comprising:

(a) a source of a silicon oxide, and optionally a source of germanium oxide or combination thereof;

(b) a source of aluminum oxide, and optionally a source of boron oxide, gallium oxide, hafnium oxide, iron oxide, tin oxide, titanium oxide, indium oxide, vanadium oxide, zirconium oxide, or combination or mixture thereof; and (c) a source of a zinc oxide;

(d) a mineralizing agent; and (e) an organic structure directing agent (OSDA) comprising a trialkyladamantylammonium cation of Formula (II) or an optionally substituted trialkylbenzylammonium cation of Formula (III):

Still further embodiments include those where the quaternary piperidinium cation of Formula (I) is or comprises cis-N,N-dialkyl-3,5-lupetidinium cation, trans-N,N-dialkyl-3,5-lupetidinium cation, cis-N,N-dialkyl-2,6-lupetidinium cation, trans-N,N-dialkyl-2,6-lupetidinium cation or a combination thereof:

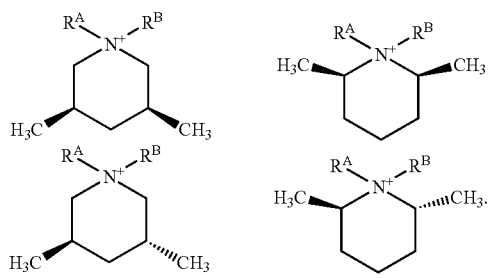

Including those wherein $R^A$ and $R^B$ are both methyl.

In other embodiments, the quaternary piperidinium cation of Formula (I) comprise a mixture of cis-N,N-dimethyl-3,

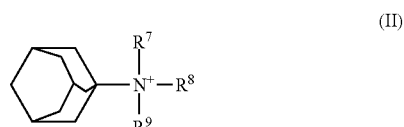

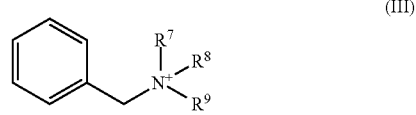

under conditions effective to crystallize a crystalline microporous zincoaluminosilicate solid of CHA topology;
wherein:
$R^7$, $R^8$, and $R^9$ are independently $C_{1-6}$ alkyl or $C_{1-3}$ alkyl.

Each of the trialkyladamantylammonium cation or optionally substituted trialkylbenzylammonium cation of Formulae (II) and (III), respectively are considered independent embodiments. The phenyl group of the trialkylbenzylammonium cation may be optionally substituted with independently one to three fluoro or optionally fluorinated or perfluorinated $C_{1-3}$ alkyl groups. In this context, the term optionally fluorinated or perfluorinated $C_{1-3}$ alkyl groups refers to —$CH_nF_{3-n}$ (methyl, n=0 to 3), —$C_2H_nF_{5-n}$ (ethyl, n=0 to 5), and —$C_3H_nF_{7-n}$ (propyl and isopropyl, n=0 to 7).

In certain of these embodiments, this phenyl group is unsubstituted.

Additional embodiments of these processes include the use of the compounds of Formula (II) or (III), wherein at least one of $R^7$, $R^8$, or $R^9$ is methyl or ethyl. In certain embodiments, at least one of $R^7$, $R^8$, or $R^9$ is methyl. In other embodiment, $R^7$, $R^8$, and $R^9$ are methyl.

In certain embodiments, the quaternary trialkyladamantyl- or trialkylbenzyl-ammonium cation has an associated bromide, chloride, fluoride, iodide, nitrate, or hydroxide anion. In other embodiments, the quaternary cation has an associated fluoride or hydroxide ion preferably substantially free of other halide counterions. In other Embodiments, the associated anion is hydroxide.

Other OSDAs known to be useful in the formation of CHA-type material include:

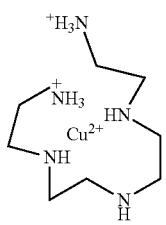

$Cu^{II}$-tetraethylenepentamine

Having now discovered the process conditions capable of producing zincoaluminosilicates having a CHA topologies, it is possible or likely that these OSDAs may be operable under the same conditions. Accordingly, the use of these OSDAs under the process conditions described here for the formation of zincoaluminosilicates having a CHA topologies are also considered embodiments of the present invention Further Aspects of Processing—Characteristics of the Ingredients and Processing Conditions.

As described above, the hydrothermal processes for preparing the crystalline microporous zincoaluminosilicate solid of AEI, CHA, or GME topology require, inter alia:
(a) a source of a silicon oxide, and optionally a source of germanium oxide or combination thereof;
(b) a source of aluminum oxide, and optionally a source of boron oxide, gallium oxide, hafnium oxide, iron oxide, tin oxide, titanium oxide, indium oxide, vanadium oxide, zirconium oxide, or combination or mixture thereof and
(c) a source of a zinc oxide.

The processes comprise composition having at least a source of silicon oxide, a source of aluminum oxide, and a source of zinc oxide. That is, in certain subsets of these embodiments, the composition is absent any source of one or more of boron oxide, gallium oxide, germanium oxide, hafnium oxide, iron oxide, tin oxide, titanium oxide, indium oxide, vanadium oxide, or zirconium oxide.

In some embodiments, the sources of aluminum oxide, silicon oxide, zinc oxide, or optional source of boron oxide, gallium oxide, germanium oxide, hafnium oxide, iron oxide, tin oxide, titanium oxide, indium oxide, vanadium oxide, zirconium oxide, or combination or mixture thereof comprises an alkoxide, hydroxide, oxide, mixed metal oxide, or combination thereof.

The processes are described thus far in terms of "a source of a silicon oxide, and optionally a source of germanium oxide or combination thereof" The use of a source of silicon oxide, germanium oxide, and any combination thereof represent individual and independent embodiments. The presence of a source of silicon oxide, either by itself or in combination with sources of germanium oxide is preferred. In some embodiments, the source of silicon oxide may comprise amorphous silica, an aluminosilicate, a zincoaluminosilicate, zincosilicate, a silicate, silica hydrogel, silicic acid, fumed silica, colloidal silica, tetra-alkyl orthosilicate, a silica hydroxide, a silicon alkoxide, or combination thereof. Sodium silicate or tetraorthosilicates are preferred sources.

The source of aluminum oxide is or comprises an alkoxide, hydroxide, or oxide of aluminum, a sodium aluminate, an aluminum siloxide, an aluminosilicate, a zincoaluminosilicate, zincoaluminate or combination thereof. In some embodiments, a mesoporous or zeolite aluminosilicate material may be used as a source of both aluminum oxide and silicon oxide. For example, FAU type zeolites serve as useful precursors.

The source of zinc oxide is or comprises a zinc(II) dicarboxylate, zinc(II) halide, zinc(II) hydroxide, zinc(II) oxide, zinc(II)nitrate, zincosilicate, zincoaluminate or zincoaluminosilicate.

As should be apparent, in some embodiments, the sources of silicon oxide, aluminum oxide, and zinc oxide may derive from common sources, for example, an aluminosilicate, a zincoaluminate, a zincosilicate, or a zincoaluminosilicate. Given the novelty of the zincoaluminosilicate compositions described in this disclosure, it should be appreciated that in such embodiments, the zincosilicate, zincoaluminate or zincoaluminosilicate may be of a topology or composition different than the topology or composition of the intended product (e.g., different than the AEI, CHA, or GME topology eventually prepared and/or isolated, for example, as a Zn—Al-containing siliceous FAU-zeolite source). In other embodiments, the zincosilicate, zincoaluminate or zincoaluminosilicate is the same topology or composition as the topology or composition of the intended product, for example, acting as seeds.

In some processes (and corresponding compositions), the source of silicon oxide is or comprises sodium silicate, the source of Al is or comprises a FAU-zeolite, and the source of zinc oxide is or comprises zinc acetate. In related embodiments, the sources of the silicon oxide, zinc oxide, and aluminum oxide is or comprises a Zn—Al-containing FAU molecular sieve.

Thus far, the processes (and associated compositions) have been described as in terms of the use or presence of a mineralizing agent Such a mineralizing agent typically comprises an aqueous hydroxide derived from an alkali metal or alkaline earth metal hydroxide, thereby rendering these compositions alkaline. In certain aspects of this embodiment, the alkali metal or alkaline earth metal hydroxide, may include, for example, LiOH, NaOH, KOH, RbOH, CsOH, $Mg(OH)_2$, $Ca(OH)_2$, $Sr(OH)_2$, or $Ba(OH)_2$. LiOH, NaOH, or KOH appear to be preferred. In some cases, the pH of the water is in a range of from 7 to 7.5, from 7.5 to 8, from 8 to 8.5, from 8.5 to 9, from 9 to 9.5, from 9.5 to 10, from 10 to 11, from 11 to 12, from 12 to 13, from 13 to 14, or any combination of two or more of these ranges, for example, at least 11. Under these conditions, the oxide precursors can be expected to be at least partially hydrated or hydrolyzed to their hydroxide forms.

The processes and compositions may also be defined in terms of the ratios of the individual ingredients. In certain embodiments, the molar ratio of Al:Si is in a range of 0.005 to 0.2 (or the molar ratio of Si:Al is in a range of from 5 to 200). In certain specific embodiments, the molar ratio of Al:Si is in a range of from 0.005 to 0.01, from 0.01 to 0.02, from 0.02 to 0.03, from 0.03 to 0.05, from 0.05 to 0.06, from 0.06 to 0.07, from 0.07 to 0.08, from 0.08 to 0.09, from 0.09 to 0.1, from 0.1 to 0.11, from 0.11 to 0.12, from 0.12 to 0.13, from 0.13 to 0.14, from 0.14 to 0.15, from 0.15 to 0.16, from 0.16 to 0.17, from 0.17 to 0.18, from 0.18 to 0.2, or any combination of two or more of these ranges, for example from 0.04 to 0.1. Again, the initial ratios of precursors will, at least in part, define the stoichiometries of the final crystalline materials. The person of skill in the art, using the teachings provided herein would be able to define the specific final stoichiometries of interest without undue experimentation. It should be appreciated that while these stoichiometries are defined solely in terms of Si and Al, some portion or all of the Si content may be substituted by Ge, and some portion of the Al may be substituted by B, Ga, Hf, Fe, Sn, Ti, In, V, or Zr.

In certain embodiments, the molar ratio of the respective OSDA (i.e., of Formula (I), (II), or (III)):Si is in a range of 0.1 to 0.75. In certain specific embodiments, the molar ratio of OSDA:Si is in a range of from 0.1 to 0.12, from 0.12 to 0.14, from 0.14 to 0.16, from 0.16 to 0.18, from 0.18 to 0.2, from 0.2 to 0.22, from 0.22 to 0.24, from 0.24 to 0.26, from 0.26 to 0.28, from 0.28 to 0.3, from 0.3 to 0.32, from 0.32 to 0.34, from 0.34 to 0.36, from 0.36 to 0.38, from 0.38 to 0.4, from 0.4 to 0.42, from 0.42 to 0.44, from 0.44 to 0.46, from 0.46 to 0.48, from 0.48 to 0.5, from 0.5 to 0.52, from 0.52 to 0.54, from 0.54 to 0.56, from 0.56 to 0.58, from 0.58 to 0.6, from 0.6 to 0.63, from 0.63 to 0.66, from 0.66 to 0.69, from 0.69 to 0.72, from 0.72 to 0.75, or any combination of two or more of these ranges, for example from 0.1 to 0.5. Again, while described in terms of Si alone, in additional embodiments, the reference to Si may also refer to the presence of Si, Ge, or both, such that the named proportion of Si refers to the combined amounts of Si and Ge.

In other embodiments, the molar ratio of water:Si is in a range of 5 to 50. In certain specific embodiments, the molar ratio of water:Si is in a range of from 5 to 6, from 6 to 7, from 7 to 8, from 8 to 9, from 9 to 10, from 10 to 11, from 11 to 12, from 12 to 13, from 13 to 14, from 14 to 15, from 15 to 16, from 16 to 17, from 17 to 18, from 18 to 19, from 19 to 20, from 20 to 22, from 22 to 24, from 24 to 26, from 26 to 28, from 28 to 30, from 30 to 32, from 32 to 34, from 34 to 36, from 36 to 38, from 38 to 40, from 40 to 42, from 42 to 44, from 44 to 46, from 46 to 48, from 48 to 50, or any combination of two or more of these ranges, for example from 10 to 50 or from 10 to 25. Again, while these ratios are described in terms of Si alone, in additional embodiments, these ratios may also refer to the presence of Si, Ge, or both, such that the named proportion of Si refers to the combined amounts of Si and Ge.

In other embodiments, the molar ratio of total hydroxide:Si is in a range of 0.1 to 1.25. As used herein, the term "total hydroxide" includes the amount of hydroxide introduced with the OSDA and separately added. In certain specific embodiments, the molar ratio of water:Si is in a range of from 0.1 to 0.15, from 0.15 to 0.2, from 0.2 to 0.25, from 0.25 to 0.3, from 0.3 to 0.35, from 0.35 to 0.4, from 0.4 to 0.45, from 0.45 to 0.5, from 0.5 to 0.6, from 0.6 to 0.65, from 0.65 to 0.7, from 0.7 to 0.75, from 0.75 to 0.8, from 0.8 to 0.85, from 0.85 to 0.9, from 0.9 to 0.95, from 0.95 to 1, from 1 to 1.05, from 1.05 to 1.1, from 1.1 to 1.15, from 1.15 to 1.2, from 1.2 to 1.25, or any combination of two or more of these ranges, for example from 0.4 to 1. Again, while these ratios are described in terms of Si alone, in additional embodiments, these ratios may also refer to the presence of Si, Ge, or both, such that the named proportion of Si refers to the combined amounts of Si and Ge.

In other embodiments, the molar ratio of Zn:Si is in a range of from 0.01 to 0.2. In specific aspects of this, the molar ratio of Zn:Si is in a range of from 0.01 to 0.02, from 0.02 to 0.03, from 0.03 to 0.05, from 0.05 to 0.06, from 0.06 to 0.07, from 0.07 to 0.08, from 0.08 to 0.09, from 0.09 to 0.1, from 0.1 to 0.11, from 0.11 to 0.12, from 0.12 to 0.13, from 0.13 to 0.14, from 0.14 to 0.15, from 0.15 to 0.16, from 0.16 to 0.17, from 0.17 to 0.18, from 0.18 to 0.2, or any combination of two or more of these ranges, for example from 0.01 to 0.1. Again, while these ratios are described in terms of Si alone, in additional embodiments, these ratios may also refer to the presence of Si, Ge, or both, such that the named proportion of Si refers to the combined amounts of Si and Ge.

The hydrothermal treating is typically done at a temperature in a range of from about 100° C. to about 200° C. for a time effective for crystallizing the respective crystalline microporous zincoaluminosilicate solid. Independent embodiments include those where the hydrothermal treating is done at at least one temperature in a range of from about 100° C. to 120° C., from 120° C. to 140° C., from 140° C. to 160° C., from 160° C. to 180° C., from 180° C. to 200° C., or any combination of two or more of these ranges. In certain specific embodiments, the temperature is in a range of from 120° C. to 180° C. These ranges provide for convenient reaction times, though higher and lower temperatures may also be employed. In some embodiment, these temperatures are applied for times in a range of from 1 hour to 14 days. Again, longer or shorter times may also be employed. This hydrothermal treating is also typically done in a sealed autoclave, at autogenous pressures. Some exemplary reaction conditions are provided in the Examples.

Once the initial zincoaluminosilicate solids are prepared, the processes include embodiments further comprising isolating these solids. These crystalline solids may be removed from the reaction mixtures by any suitable means (e.g., filtration, centrifugation, etc.), washed, and dried. Such drying may be done in air at temperatures ranging from 25° C. to about 200° C. Typically, such drying is done at a temperature of about 100° C.

These crystalline microporous zincoaluminosilicate solids may be further modified, for example, by incorporating metals with the pore structures, either before or after drying, for example by replacing some of the cations in the structures with additional metal cations using techniques known to be suitable for this purpose (e.g., ion exchange). Such cations can include those of rare earth, Group 1, Group 2 and Group 8 metals, for example Li, K, Na, Ca, Cd, Co, Cu, Fe, Mg, Mn, Ni, Pt, Pd, Re, Sn, Ti, V, W, Zn and their mixtures.

Where the isolated solid is a zincoaluminosilicate of AEI or CHA topology, further processing of these materials, whether modified or not, may comprise heating the isolated crystalline microporous zincoaluminosilicate solid at a temperature in a range of from about 250° C. to about 600° C. to form an OSDA-depleted zincoaluminosilicate product. This calcining step may be carried out by holding the crystalline microporous solid at at least one or more temperatures. In some cases two or more temperatures, in a range of from 350° C. to 400° C., from 400° C. to 450° C., from 450° C. to 500° C., from 500° C. to 550° C., from 550° C. to 600° C., or any combination of two or more of these ranges may be employed. In certain specific embodiments, where the product is a zincoaluminosilicate solid of GME topology, the temperature range is from about 250° C. to about 400° C. In either case, the heating may be done in an oxidizing atmosphere, such as air or oxygen, or in the presence of other oxidizing agents. In other embodiments, the heating is done in an inert atmosphere, such as argon or nitrogen.

In those embodiments where the processing involved heating, typical heating rates include is 0.1° C. to 10° C. per minute and or 0.5° C. to 5° C. per minute. Different heating rates may be employed depending on the temperature range. Depending on the nature of the calcining atmosphere, the materials may be heated to the indicated temperatures for periods of time ranging from 1 to 60 hours or more, to produce a catalytically active product.

As used herein, the term "OSDA-depleted" (or composition having depleted OSDA) refers to a composition having a lesser content of OSDA after the treatment than before. In preferred embodiments, substantially all (e.g., greater than 90, 95, 98, 99, or 99.5 wt %) or all of the OSDA is removed by the treatment; in some embodiments, this can be confirmed by the absence of a TGA endotherm associated with the removal of the OSDA when the product material is subject to TGA analysis or the absence or substantial absence of C or N in elemental analysis (prior to heating, expect composition to comprise C, N, O, Si, Al, H, and optionally Li, Na, K).

Further processing of these materials, whether modified or not, may also comprise contacting the isolated crystalline microporous zincoaluminosilicate solid with ozone or other oxidizing agent at a temperature in a range of 100° C. to 200° C. for a time sufficient to form an OSDA-depleted zincoaluminosilicate product. In certain of these embodiments, the heating is done at a temperature of about 150° C. to form an OSDA-depleted product. The ozone-treatment can be carried out in a flow of ozone-containing oxygen (typically for 6 hours or more. but shorter could be feasible). Any oxidative environment treatment sufficient to remove the OSDA can be used. Such environments, for example, can involve the use of organic oxidizers (alkyl or aryl peroxides or peracids) or inorganic peroxides (e.g., $H_2O_2$) (alkyl or aryl peroxides or peracids.

Where the isolated solid is a zincoaluminosilicate of GME topology, further processing of these materials, whether modified or not, may also comprise, heating the isolated crystalline microporous zincoaluminosilicate solid at a temperature in a range of from about 200° C. to about 600° C. in the presence of an alkali, alkaline earth, transition metal, rare earth metal, ammonium or alkylammonium salts (anions including halide, preferable chloride, nitrate, sulfate, phosphate, carboxylate, or mixtures thereof) to form a dehydrated or an OSDA-depleted product. In certain of these embodiments, the heating is done in the presence of NaCl or KCl. In certain exemplary embodiments, the heating is done at a temperature in a range of from 500 to 600° C. In exemplary embodiments, the heating is done in either an oxidizing or inert atmosphere.

Such use of salts is consistent with the disclosures provided in US Patent Appl. Publ. No. 2002/0119887 to Q. Huo and N. A. Stephenson. For water removal, the zincoaluminosilicate of GME topology is typically heated to 350° C. For substantial OSDA removal, temperatures up to 500° C. are typically employed. As described in Huo, the preferred salts include alkali metal (Li, Na, K, Rb, Cs) halides (preferably CO; alkaline earth (Be, Mg, Ca, Sr, Ba) nitrates or phosphates; aluminum, gallium, and indium carbonates; zinc sulfate; Ag, Cd borate or silicate; Ru, Rh, Pd, Pt, Au, or Hg carboxylates; La, Ce, Pr, Nd, Pm, or Sm sulfonates; Eu, Gd alkoxide; $R_{4-n}N^+H_n$ phenolates, where R is alkyl, n=0-4—as described in Huo. In some cases, the excess salt or salts can be removed, following calcination, by water (or other solvent) rinse or in a combination with ion-exchange and subsequent desolvation.

Once dehydrated or calcined, the dehydrated or OSDA-depleted crystalline microporous material may be treated with an aqueous ammonium or metal salt or may be treated under conditions so as to incorporate at least one type of alkaline earth metal or alkaline earth metal oxide or salt, or transition metal or transition metal oxide. In some embodiments, the salt is a halide salt. Where the salt is an ammonium salt, the resulting zincoaluminosilicate contains the ammonium cation which, after calcination, decomposes to provide the protonated zincoaluminosilicate. In other embodiments, the metal salt comprises one or more of $K^+$, $Li^+$, $Na^+$, $Rb^+$, $Cs^+$: $Co^{2+}$, $Ca^{2+}$, $Mg^{2+}$, $Sr^{2+}$; $Ba^{2+}$; $Ni^{2+}$; or $Fe^{2+}$. In other specific embodiments, the metal cation salt is a copper salt, for example, Schweizer's reagent (tetra-aminediaquacopper dihydroxide, $[Cu(NH_3)_4(H_2O)_2](OH)_2]$), copper(II) nitrate, copper (II) diacetate (or other dicarboxylate), or copper(II) carbonate.

The addition of a transition metal or transition metal oxide may be accomplished, for example by chemical vapor deposition or chemical precipitation. As used herein, the term "transition metal" refers to any element in the d-block of the periodic table, which includes groups 3 to 12 on the periodic table. In actual practice, the f-block lanthanide and actinide series are also considered transition metals and are called "inner transition metals. This definition of transition metals also encompasses Group 4 to Group 12 elements. In certain independent embodiments, the transition metal or transition metal oxide comprises an element of Groups 6, 7, 8, 9, 10, 11, or 12. In other independent embodiments, the transition metal or transition metal oxide comprises scandium, yttrium, tin, titanium, zirconium, vanadium, manganese, chromium, molybdenum, tungsten, iron, ruthenium, osmium, cobalt, rhodium, iridium, nickel, palladium, platinum, copper, silver, gold, or mixtures. Fe, Ru, OS, Co, Rh, Ir, Ni, Pd, Pt, Cu, Ag, Au, and mixtures thereof are preferred.

Intermediate Reaction Compositions

As described herein, the as-formed and post-treated crystalline zincoaluminosilicate compositions themselves are within the scope of the present disclosure and are considered to be independent embodiments of the present invention. All of the descriptions used to describe the features of the inventive processes are also considered to apply to these compositions. In an abundance of caution, some of these are presented here, but these descriptions should not be considered to exclude embodiments provided elsewhere.

Included in these embodiments are the compositions comprising the aqueous compositions used in the hydrothermal treatments together with the respective crystalline microporous zincoaluminosilicate products, wherein the zincoaluminosilicate products contain the respective OSDAs used in their preparation occluded in their pores.

For example, in some embodiments, the composition comprises:

(a) a source of a silicon oxide, and optionally a source of germanium oxide, or combination thereof;

(b) a source of aluminum oxide, and optionally a source of boron oxide, gallium oxide, hafnium oxide, iron oxide, tin oxide, titanium oxide, indium oxide, vanadium oxide, zirconium oxide, or combination or mixture thereof; and (c) a source zinc oxide;

(d) a mineralizing agent;

(e) an organic structure directing agent (OSDA) comprising at least one isomer of the quaternary piperidinium cation of Formula (I) (or any of the embodied cations of Formula (I) described elsewhere in this disclosure);

and (f) a compositionally consistent crystalline microporous zincoaluminosilicate solid of an AEI or GME topology.

In other embodiments, such a composition comprises:

(a) a source of a silicon oxide, and optionally a source of germanium oxide or combination thereof;

(b) a source of aluminum oxide, and optionally a source of boron oxide, gallium oxide, hafnium oxide, iron oxide, tin oxide, titanium oxide, indium oxide, vanadium oxide, zirconium oxide, or combination or mixture thereof; and (c) a source of a zinc oxide;

(d) a mineralizing agent; and (e) an organic structure directing agent (OSDA) comprising a trialkyladamantylammonium cation of Formula (II) or an optionally substituted trialkylbenzylammonium cation of Formula (III) (or any of the embodied cations of Formulae (II) or (III) described elsewhere in this disclosure):

and (f) a compositionally consistent crystalline microporous zincoaluminosilicate solid of an AEI or GME topology.

As used herein, the term "compositionally consistent" refers to a crystalline zincoaluminosilicate composition having a stoichiometry resulting from the crystallization of the sources of oxides in the presence of the respective OSDAs; e.g., the OSDAs of Formula (I) for the zincoaluminosilicate having AEI or GME topologies or the OSDAs of Formula (II) or (III) for the zincoaluminosilicate having CHA topology. In some of these embodiments, for example, this term reflects a composition which is the result of at least a partial progression of the hydrothermal treating process used to prepare these materials. Typically, these compositionally consistent crystalline microporous zincoaluminosilicate solids contain, occluded in their pores, the OSDAs used to make them; i.e., the OSDAs present in the associated aqueous compositions, and such is within the scope of the present disclosure. In separate embodiments, these compositionally consistent crystalline microporous zincoaluminosilicate solids may also be substantially free of the OSDAs used in the aqueous media; in such embodiments, the zincoaluminosilicate may be used as seed material for the crystallization.

These compositions may comprise any of the types and ratios of ingredients, and may exist at temperatures consistent with the processing conditions described above as useful for the hydrothermal processing. It should be appreciated that this disclosure captures each and every of these permutations as separate embodiments, as if they were separately listed. In some embodiments, these compositions exist in the form of a gel.

Crystalline Microporous Compositions

In addition to the processing and process compositions, the microcrystalline products resulting from the further processing of the initially prepared materials are also considered within the scope of the present invention. Accordingly, in some embodiments, the various compositionally consistent crystalline microporous zincoaluminosilicate solid of AEI, CHA, or GME topologies are isolated solids; i.e., they exist in the absence of the aqueous hydrothermal treatment media used to produce them. These isolated microporous zincoaluminosilicate solid of AEI, CHA, or GME topologies may contain the any of the corresponding OSDAs described herein occluded in their pores—i.e., the OSDAs of Formula (I) within the frameworks of the zincoaluminosilicates having AEI or GME topologies or the OSDAs of Formula (II) or (III) within the frameworks of the zincoaluminosilicates having AEI or GME topologies—or they may be devoid or substantially devoid of such organic materials (the terms "devoid" and "substantially devoid" being quantitatively analogous to the term "OSDA depleted").

The presence of the OSDAs may be identified using, for example $^{13}$C NMR or any of the methods defined in the Examples. It is a particular feature of the present invention that the cationic OSDAs retain their original structures, including their stereochemical conformations during the synthetic processes, these structures being compromised during the subsequent calcinations.

More specifically, some embodiments provide crystalline microporous zincoaluminosilicate solids of GME or AEI topology having pores at least some of which are occluded with quaternary piperidinium cations of Formula (I), in any of the embodiments described herein for these cations. In other embodiments, the pores are substantially OSDA-depleted.

Such zincoaluminosilicate solids of GME or AEI topology may also be described in terms of their Si:Al and Si:Zn molar ratios, as well as their physical characteristics. In certain embodiments, the crystalline microporous zincoaluminosilicate solid having a GME or AEI topology are characterized as having a molar ratio of Si:Al in a range of from 3 to about 200 (or $SiO_2/Al_2O_3$ ratio of from 6 to 400) and molar ratio of Si:Zn in a range of from 5 to 50. Aspects of this embodiment includes those where the molar ratio of Si:Al is in a range of from 3 to 3.2, from 3.2 to 3.4, from 3.4 to 3.6, from 3.6 to 3.8, from 3.8 to 4, from 4 to 4.2, from 4.2 to 4.4, from 4.4 to 4.6, from 4.6 to 4.8, from 4.8 to 5, from 5 to 5.2, from 5.2 to 5.4, from 5.4 to 5.6, from 5.6 to 5.8, from 5.8 to 6 from 6 to 6.4, from 6.4 to 6.8, from 6.8 to 7.2, from 7.2 to 7.6, from 7.6 to 8, from 8 to 8.4, from 8.4 to 8.8, from 8.8 to 9.2, from 9.2 to 9.6 from 9.6 to 10, from 10 to 10.4, from 10.4 to 10.8, from 10.8 to 11.2, from 11.2 to 11.6, from 11.6 to 12, from 12 to 12.4, from 12.4 to 12.8, from 12.8 to 13.2, from 13.2 to 13.6, from 13.6 to 14, from 14 to 14.4, from 14.4 to 14.8, from 14.8 to 15.2, from 15.2 to 15.4, from 15.5 to 15.8, from 15.8 to 16.2, from 16.2 to 16.6, from 16.6 to 17, from 17 to 17.4, from 17.4 to 17.8, from 17.8 to 18.2, from 18.2 to 18.6, from 18.6 to 19, from 19 to 19.4, from 19.4 to 19.8, from 19.8 to 20, from 20 to 25, from 25 to 30, from 30 to 35, from 35 to 40, from 40 to 45, from 45 to 50, from 50 to 60, from 60 to 70, from 70 to 80, from 80 to 90, from 90 to 100, from 100 to 120, from 120 to 140, from 140 to 160, from 160 to 180, from 180 to 200, or any combination of two or more of these ranges, including for example, from 3.6 to 15, from 5 to 10, from 3 to 20, from 3 to 50. Other aspects include those where the molar ratio of Si:Zn is in a range of from 5 to 5.5, from 5.5 to 6, from 6 to 6.5, from 6.5 to 7, from 7 to 7.5, from 7.5 to 8, from 8 to 8.5, from 8.5 to 9, from 9 to 9.5, from 9.5 to 10, from 10 to 11, from 11 to 12, from 12 to 13, from 13 to 14, from 14 to 15, from 15 to 16, from 16 to 17, from 17 to 18, from 18 to 19, from 19 to 20, from 20 to 21, from 21 to 22, from 22 to 23, from 23 to 24, from 24 to 25, from 25 to 26, from 26 to 27, from 27 to 28, from 28 to 29, from 29 to 30, from 30 to 34, from 34 to 38, from 38 to 42, from 42 to 46, from 46 to 50, or any combination of two or more of these ranges, including for example, from 8 to 26. Again, independent embodiments include the crystalline microporous zincoaluminosilicate solid having a GME or AEI topology and Si:Al and Si:Zn ratios when the pores are substantially depleted of OSDA.

Other embodiments provide crystalline microporous zincoaluminosilicate solids of CHA topology having pores at least some of which are occluded with quaternary piperidinium cations of Formula (II) or (III), in any of the embodiments described herein for these cations. In other embodiments, the pores are substantially OSDA-depleted.

Such zincoaluminosilicate solids of CHA topology may also be described in terms of their Si:Al and Si:Zn ratios, as well as their physical characteristics. In certain embodiments, the crystalline microporous zincoaluminosilicate solid having a CHA topology are characterized as having a molar ratio of Si:Al in a range of from 4 to 100 (or $SiO_2/Al_2O_3$ ratio from 8 to 200) and a molar ratio of Si:Zn in a range from 5 to 50. Aspects of this embodiment includes those where the molar ratio of Si:Al is in a range of from 4 to 5, from 5 to 6, from 6 to 8, from 8 to 10, 10 to 12, from 12 14, from 14 to 16, from 16 to 18, from 18 to 20, from 20 to 22, from 22 to 24, from 24 to 26, from 26 to 28, from 28 to 30, from 30 to 32, from 32 to 34, from 34 to 36, from 36 to 38, from 38 to 40, from 40 to 50, from 50 to 60, from 60 to 70, from 70 to 80, from 80 to 90, from 90 to 100, or any combination of two or more of these ranges, including for example, from 4 to 12 or 6 to 10. Other aspects include those where the molar ratio of Si:Zn is in a range of from 5 to 6, from 6 to 7, from 7 to 8, from 8 to 9, from 9 to 10, from 10 to 12, from 12 to 14, from 14 to 16, from 16 to 18, from 18 to 20, from 20 to 22, from 22 to 24, from 24 to 26, from 26 to 28, from 28 to 30, from 30 to 32, from 32 to 34, from 34 to 36, from 36 to 38, from 38 to 40, from 40 to 42, from 42 to 44, from 44 to 46, from 46 to 48, from 48 to 50, or any combination of two or more of these ranges, including for example, from 18 to 36 or from 20 to 30. Again, independent embodiments include the crystalline microporous zincoaluminosilicate solid having a CHA topology and Si:Al and Si:Zn ratios described here when the pores are substantially depleted of OSDA.

Figure 3:
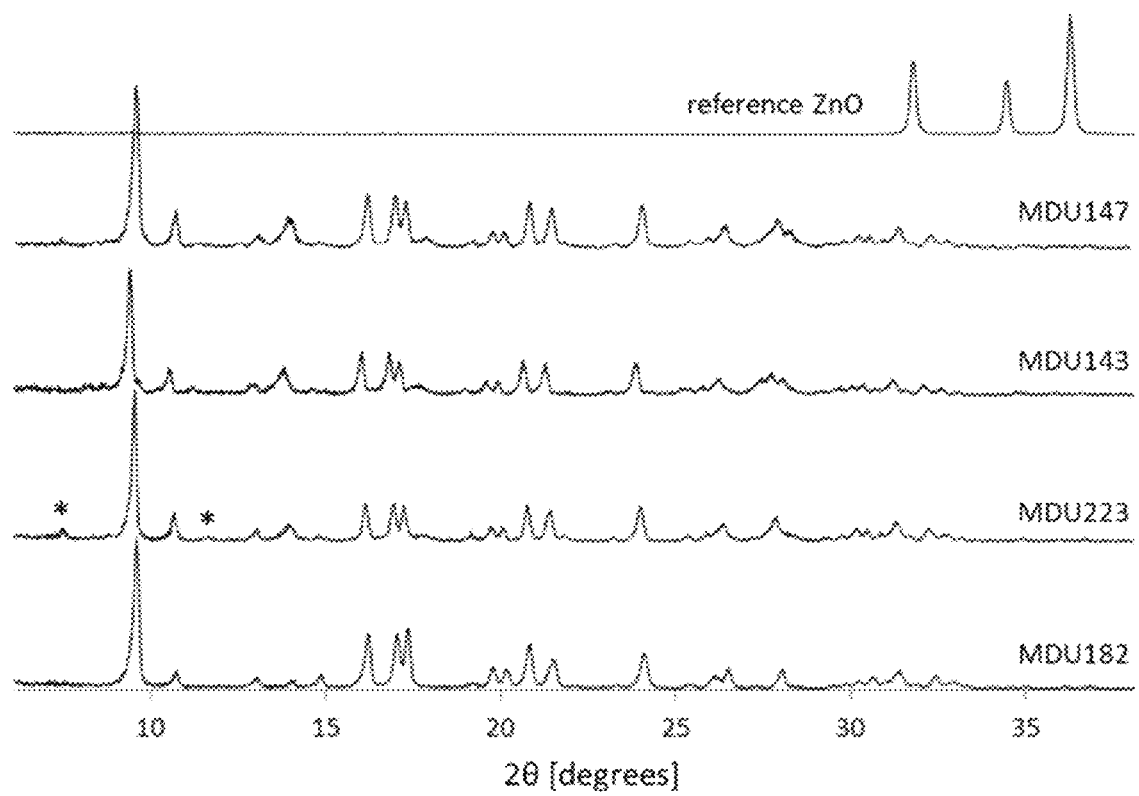
FIG. 3 shows PXRD traces of as-made AEI phases produced in different gels according to Table 1. *GME impurity. Note that mdu182 is a pure aluminosilicate AEI: SSZ-39.
Figure 4:
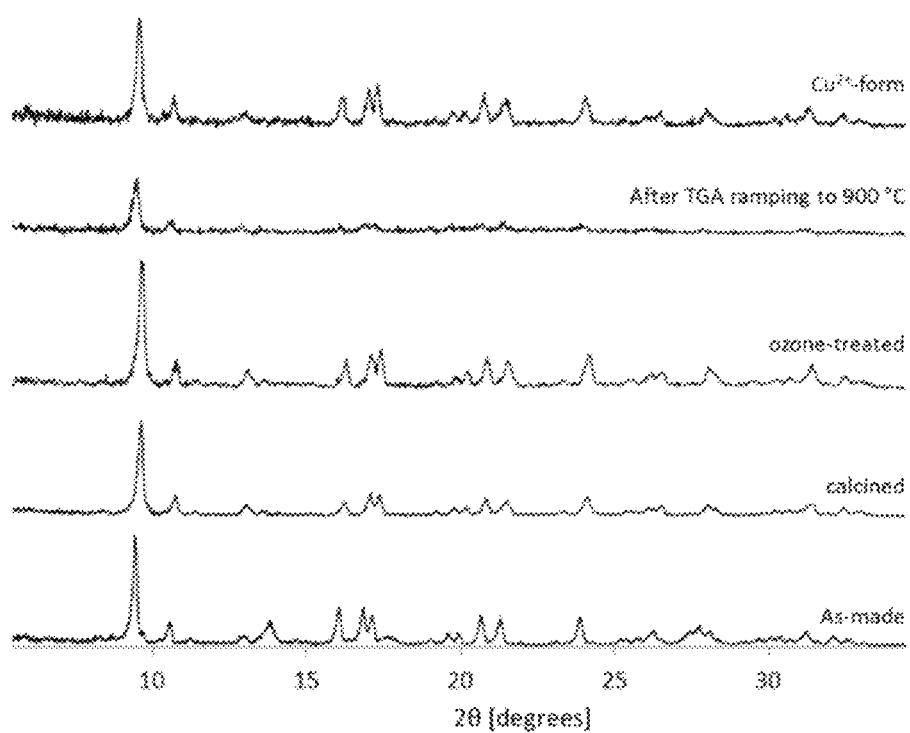
FIG. 4 shows PXRD traces of Zn—Al-AEI material produced in synthesis MDU143 after various treatments.
Figure 9:
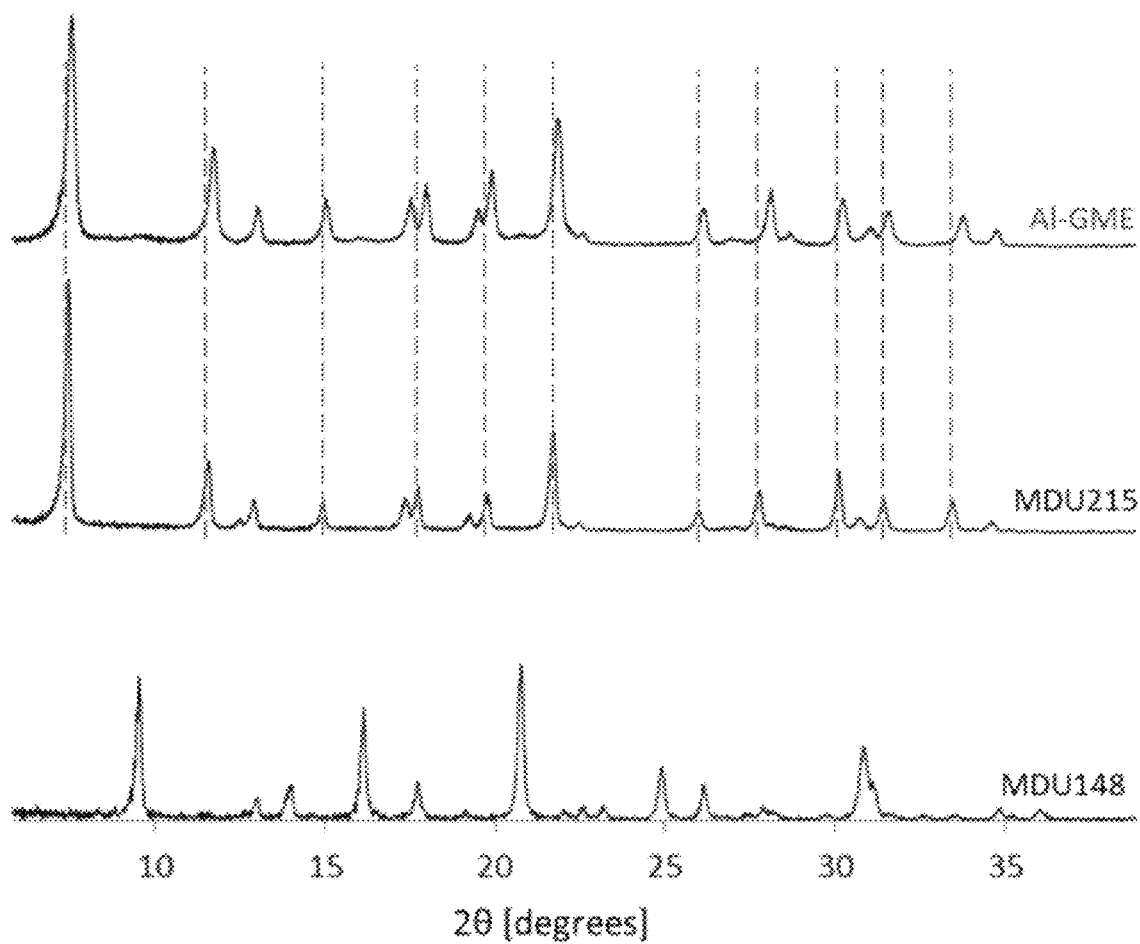
FIG. 9 shows PXRD traces of as-made Zn—Al-CHA and Zn—Al-GME phases produced in different gels according to Table 1 and a aluminosilicate GME comparison

The crystalline microporous zincoaluminosilicate solids may also characterized by their physical properties. In certain embodiments, these zincoaluminosilicate solid exhibit at least one of the following:

(a) an X-ray diffraction (XRD) pattern the same as or consistent with any one of those shown in FIG. 3 (Zn—Al-AEI), FIG. 4 (Zn—Al-AEI), or FIG. 9 (Zn—Al-GME and Zn—Al-CHA);

(b) an XRD pattern having at least the five major peaks substantially as provided in Table 2 (see Example 2.1)

Figure 8:
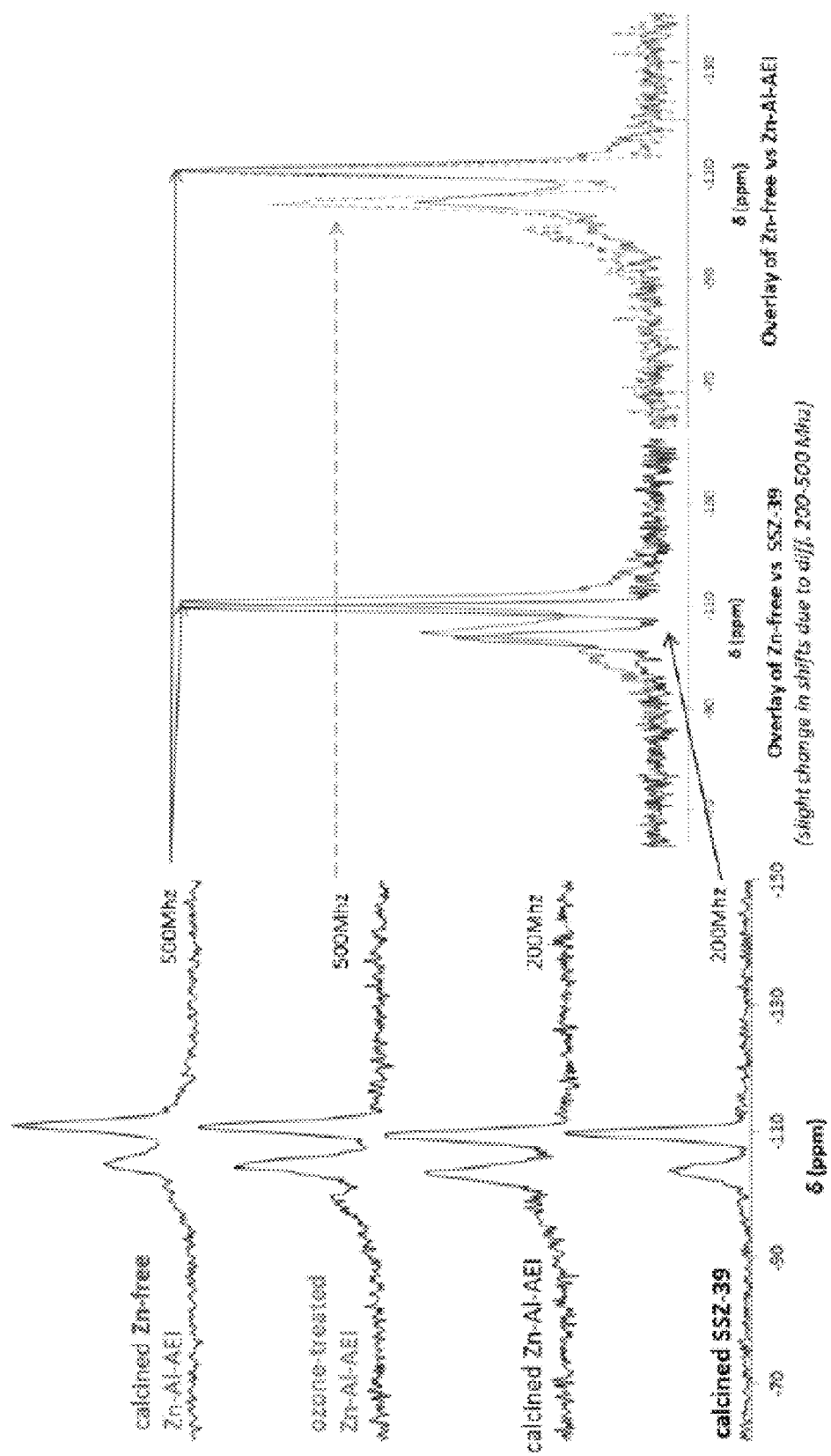
FIG. 8 shows scaled and stacked $^{29}$Si MAS (Bloch Decay) NMR spectra and crucial overlays for some of the NMR spectra from FIG. 7.

(c) an $^{29}Si$ MAS spectrum for having a plurality of chemical shifts of about −110.5, −105, −99.5 ppm downfield of a peak corresponding to and external standard of tetramethylsilane (for Zn—Al-AEI); or (d) an $^{29}Si$ MAS spectrum the same as or consistent with the one shown in FIG. 8 for Zn—Al-AEI.

Figure 5:
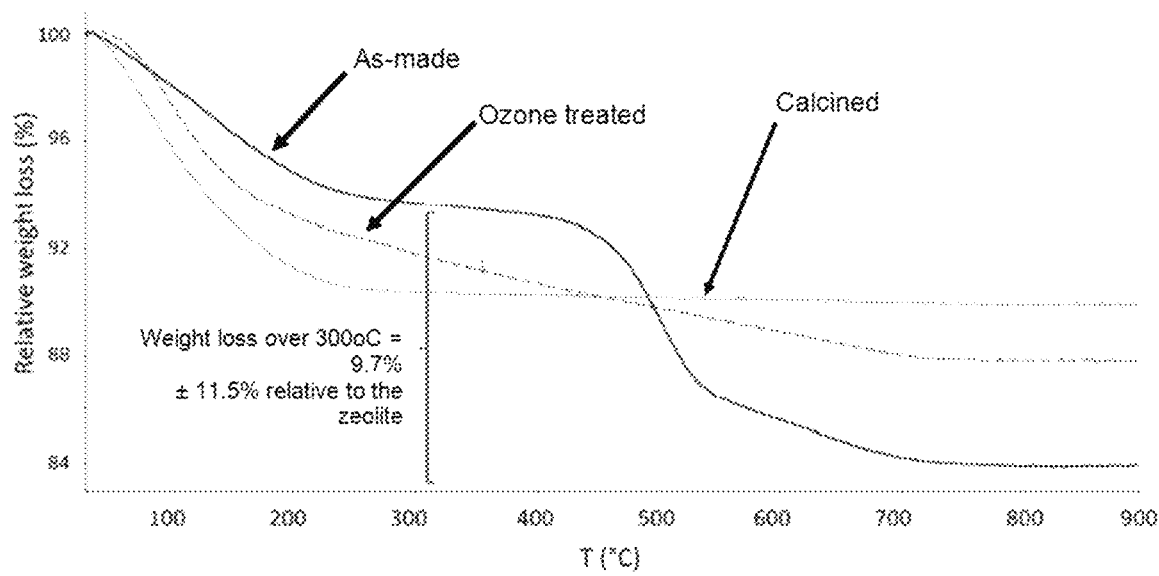
FIG. 5 shows TGA analyses of MDU143-materials: as made, ozone-treated and calcined.

Additional embodiments include those Zn—Al-AEI compositions exhibit (e) a thermogravimetric analysis (TGA) curve the same as or consistent with the one shown in FIG. 5 (for Zn—Al-AEI) or (f); a thermogravimetric analysis (TGA) curve indicative of a loss of 8 to 20 wt %.

The disclosed crystalline microporous zincoaluminosilicate compositions include those which result from the post-treatment or further processing described in the processing section. These include those zincoaluminosilicates which are in their hydrogen forms or have cations, metals or metal oxides within their pore structures. Accordingly, in certain embodiments, the microporous zincoaluminosilicate solids having AEI, CHA, and GME topologies, contain Li, Na, K, Rb, Cs, Be, Mg, Ca, Sr, Ba, Al, Ga, In, Zn, Ag, Cd, Ru, Rh, Pd, Pt, Au, Hg, La, Ce, Pr, Nd, Pm, Sm, Eu, or $R_{4-n}N^+H_n$ cations, where R is alkyl, n=0-4 in at least some of their pores. In specific aspects of these embodiments, these pores contain NaCl or KCl.

Additional embodiments include those crystalline microporous zincoaluminosilicate solids having AEI, CHA, and GME topologies, at least some of whose pores transition metals, transition metal oxides, or salts, for example scandium, yttrium, tin, titanium, zirconium, vanadium, manganese, chromium, molybdenum, tungsten, iron, ruthenium, osmium, cobalt, rhodium, iridium, nickel, palladium, platinum, copper, silver, gold, or mixtures thereof, each as a metal, oxide, or salt. In one specific embodiment, the pores of the zincoaluminosilicate solids contain copper, as cation, metal, oxide, or salt.

Use of the Inventive Compositions—Catalysis

The calcined crystalline microporous zincoaluminosilicate solids, calcined, doped, or treated with the catalysts described herein may also be used as catalysts for a variety of chemical reactions. The specific pore sizes of the AEI- and CHA-type frameworks make zincoaluminosilicates having these topologies particularly suited for their use in catalyzing reactions including carbonylating DME with CO at low temperatures, reducing NOx with methane, reducing NOx with ammonia, MTO (methanol-to-olefin), oligomerizing alkenes, aminating lower alcohols, separating and sorbing lower alkanes, converting a lower alcohol (for example, methanol, ethanol, or propanol) or other oxygenated hydrocarbon to produce an olefin products, reducing the content of an oxide of nitrogen contained in a gas stream in the presence of oxygen, or separating nitrogen from a nitrogen-containing gas mixture. Such reactions may be catalyzed by contacting the respective feedstock with a catalyst comprising one or more of the crystalline microporous zincoaluminosilicate solid having an AEI or CHA topology under conditions sufficient to affect the named transformation.

Further, since the aluminosilicate version of AEI (SSZ-39), when exchanged with $Cu^{2+}$, is reported to have excellent catalytic properties for $deNO_x$ and a reported zincoaluminophosphate AEI material (ZnAPO-18) is reported to show good MTO activity, the present zincoaluminosilicate are expected to show particular activity in these applications. Accordingly, some embodiments disclose processes comprising reducing NOx in exhaust gases by catalytic reduction (e.g., with ammonia) or converting methane via partial oxidation to methanol, for examples with $O_2$, $H_2O_2$, or $N_2O$, with a catalyst comprising a copper exchanged crystalline microporous zincoaluminosilicate solid of AEI or CHA topology, under conditions sufficient to affect the named transformation. Additional embodiments include contacting methanol with the crystalline microporous zincoaluminosilicate solid of AEI or CHA topology under conditions sufficient to convert the methanol to at least one type of olefin.

Catalysts comprising GME, having larger pore sizes, are capable of catalyzing all of the preceding reactions, as well as others, including converting methane via partial oxidation to methanol, converting methanol to at least one type of olefin, cracking, dehydrogenating, converting paraffins to aromatics, isomerizing xylenes, disproportionating toluene, alkylating aromatic hydrocarbons, hydrocracking a hydrocarbon, dewaxing a hydrocarbon feedstock, isomerizing an olefin, producing a higher molecular weight hydrocarbon from lower molecular weight hydrocarbon, or reforming a hydrocarbon. Such reactions may be catalyzed by contacting the respective feedstock with a catalyst comprising at least the crystalline microporous zincoaluminosilicate solid having GME topology under conditions sufficient to affect the named transformation. Zincoaluminosilicate solid having GME topology appear to be especially suitable for converting paraffins into aromatics (e.g., hexane to benzene) and for carbonylating DME with CO at low temperatures. The GME framework topology is also interesting for applications in sorption and catalysis. Sorption applications could potentially be found in hydrocarbon separation processes and ion-exchange. Catalytic processes of interest include, but are not limited to, the aromatization of naphtha, the dehydrocyclization of hexane, hydrocarbon isomerization and/or chlorination.

Specific conditions for many of these transformations are known to those of ordinary skill in the art. Exemplary conditions for such reactions/transformations may also be found in WO/1999/008961, and U.S. Pat. No. 4,544,538, both of which are incorporated by reference herein in its entirety for all purposes.

Depending upon the type of reaction which is catalyzed, the microporous solid may be predominantly in the hydrogen form, partially acidic or substantially free of acidity. As used herein, "predominantly in the hydrogen form" means that, after calcination (which may also include exchange of the pre-calcined material with $NH_4^+$ prior to calcination), at least 80% of the cation sites are occupied by hydrogen ions and/or rare earth ions.

Use of the Inventive Compositions—Ion Exchange

As described elsewhere herein, zincoaluminosilicates have an increased number of (divalent) exchange sites relative to aluminosilicates with the same Si/Al ratios. These properties make these zincoaluminosilicate compositions are expected to be useful in ion exchange applications.

The following listing of embodiments is intended to complement, rather than displace or supersede, any of the previous descriptions.

Embodiment 1. A process for preparing a zincoaluminosilicate composition, the process comprising hydrothermally treating an aqueous composition comprising:

(a) a source of a silicon oxide, and optionally a source of germanium oxide or combination thereof;

(b) a source of aluminum oxide, and optionally a source of boron oxide, gallium oxide, hafnium oxide, iron oxide, tin oxide, titanium oxide, indium oxide, vanadium oxide, zirconium oxide, or combination or mixture thereof; and (c) a source of a zinc oxide;

(d) a mineralizing agent; and (e) an organic structure directing agent (OSDA) comprising at least one isomer of the quaternary piperidinium cation of Formula (I):

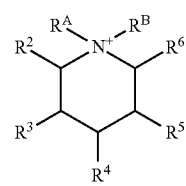

(I)

under conditions effective to crystallize a crystalline microporous zincoaluminosilicate solid of AEI or GME topology; wherein $R^A$ and $R^B$ are independently a $C_{1-3}$ alkyl, or together with the N to which they are bound form a 5 or 6 membered saturated or unsaturated ring; and $R^2$, $R^3$, $R^4$, $R^5$, and $R^6$ are independently H or $C_{1-3}$ alkyl, provided at least two of $R^2$, $R^3$, $R^4$, $R^5$, and $R^6$ are independently $C_{1-3}$ alkyl.

In some Aspects of this Embodiment, the OSDA comprises at least one isomer of the quaternary piperidinium cation of Formula (IA) or (IB):

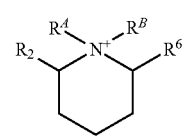

(IA)

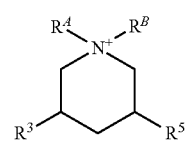

(IB)

wherein $R^2$ $R^3$, $R^5$, and $R^6$ are independently $C_{1-3}$ alkyl. In other Aspects of this Embodiment, the quaternary piperidinium cation has an associated bromide, chloride, fluoride, iodide, nitrate, or hydroxide anion.

Embodiment 2. The process of Embodiment 1, wherein the quaternary piperidinium cation of Formula (I) is or comprises an N,N-dialkyl-2,6-lupetidinium cation or an N,N-dialkyl-3,5-lupetidinium cation:

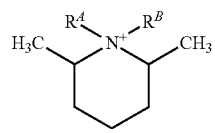 or 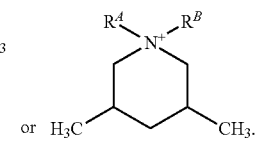

In separate Aspects of this Embodiment, the quaternary piperidinium cation of Formula (I) is an N,N-dialkyl-2,6-lupetidinium cation. In other Aspects, it is an N,N-dialkyl-3,5-lupetidinium cation.

Embodiment 3. The process of Embodiment 1 or 2, wherein the quaternary piperidinium cation of Formula (I) is or comprises cis-N,N-dialkyl-3,5-lupetidinium cation, trans-N,N-dialkyl-3,5-lupetidinium cation, cis-N,N-dialkyl-2,6-lupetidinium cation, trans-N,N-dialkyl-2,6-lupetidinium cation or a combination thereof:

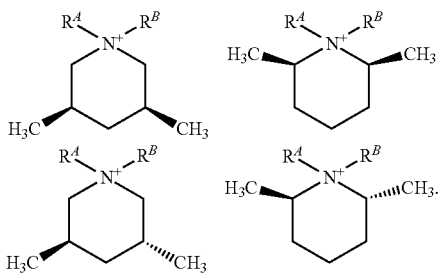

Each of these cations is an independent Aspect of this Embodiment.

Embodiment 4. The process of Embodiment 2 or 3, wherein $R^{A,}$ and $R^B$ are both methyl.

Embodiment 5. The process of any one of Embodiments 1 to 4, wherein the quaternary piperidinium cation has an associated fluoride or hydroxide ion preferably substantially free of other halide counterions. In separate Aspects of this Embodiment, the associated anion is hydroxide.

Embodiment 6. A process for preparing a zincoaluminosilicate composition of CHA topology, the process comprising hydrothermally treating an aqueous composition comprising:
(a) a source of a silicon oxide, and optionally a source of germanium oxide or combination thereof;
(b) a source of aluminum oxide, and optionally a source of boron oxide, gallium oxide, hafnium oxide, iron oxide, tin oxide, titanium oxide, indium oxide, vanadium oxide, zirconium oxide, or combination or mixture thereof; and
(c) a source of a zinc oxide;
(d) a mineralizing agent; and
(e) an organic structure directing agent (OSDA) comprising a trialkyladamantylammonium cation of Formula (II) or an optionally substituted trialkylbenzylammonium cation of Formula (III):

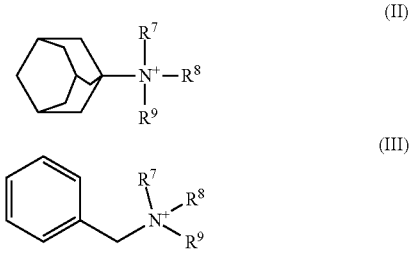

under conditions effective to crystallize a crystalline microporous zincoaluminosilicate solid of CHA topology;
wherein:
$R^7$, $R^8$, and $R^9$ are independently $C_{1-6}$ alkyl or $C_{1-3}$ alkyl; and wherein
the quaternary trialkyladamantyl- or trialkylbenzyl-ammonium cation has an associated bromide, chloride, fluoride, iodide, nitrate or hydroxide anion. Each of the trialkyladamantylammonium cation of Formula (II) or an optionally substituted trialkylbenzylammonium cation of Formula (III) are considered independent Embodiments. In certain Aspects of this Embodiment, the phenyl group of the trialkylbenzylammonium cation may be optionally substituted with independently one to three fluoro or optionally fluorinated or perfluorinated $C_{1-3}$ alkyl groups.

Embodiment 7. The process of claim 6, wherein at least one of $R^7$, $R^8$, or $R^9$ is methyl or ethyl. In certain Aspects of this Embodiment, at least one of $R^7$, $R^8$, or $R^9$ is methyl. In other Aspects of this Embodiment, each one of $R^7$, $R^8$, or $R^9$ is methyl.

Embodiment 8. The process of any one of Embodiments 1 to 7, wherein the quaternary cation has an associated fluoride or hydroxide ion preferably substantially free of other halide counterions. In some Aspects of this Embodiment, the associated anion is hydroxide.

Embodiment 9. The process of any one of Embodiments 1 to 8, wherein the composition being hydrothermally treated is or comprises a source of silicon oxide, a source of aluminum oxide, and a source of zinc oxide. In other Aspects of this Embodiment, some of the sources of silicon oxide, aluminum oxide, and zinc oxide derive from common sources, for example, an aluminosilicate, a zincoaluminate, a zincosilicate, or a zincoaluminosilicate. In other Aspects of this Embodiment, the composition is absent any source of one or more of boron oxide, gallium oxide, germanium oxide, hafnium oxide, iron oxide, tin oxide, titanium oxide, indium oxide, vanadium oxide, or zirconium oxide.

Embodiment 10. The process of any one of Embodiments 1 to 9, wherein the source of aluminum oxide, silicon oxide, zinc oxide, or optional source of boron oxide, gallium oxide, germanium oxide, hafnium oxide, iron oxide, tin oxide, titanium oxide, indium oxide, vanadium oxide, zirconium oxide, or combination or mixture thereof comprises an alkoxide, hydroxide, oxide, mixed metal oxide, or combination thereof.

Embodiment 11. The process of any one of Embodiments 1 to 10, wherein the source of silicon oxide is or comprises an aluminosilicate, a zincoaluminosilicate, zincosilicate a silicate, silica hydrogel, silicic acid, fumed silica, colloidal silica, tetra-alkyl orthosilicate, a silica hydroxide or combination thereof. Given the novelty of the zincoaluminosilicate compositions described in this disclosure, it should be appreciated that in certain Aspects of this Embodiment, the zincoaluminosilicate or zincosilicate is of a topology or composition different than the topology or composition of the intended product (e.g., different than the AEI, CHA, or GME topology eventually prepared and/or isolated). In other Aspects of this Embodiment, the zincoaluminosilicate or zincosilicate is the same topology or composition as the topology or composition of the intended product, for example, acting as seeds.

Embodiment 12. The process of any one of Embodiments 1 to 11, wherein the source of aluminum oxide is or comprises an alkoxide, hydroxide, or oxide of aluminum, a sodium aluminate, an aluminum siloxide, an aluminosilicate, a zincoaluminosilicate, zincoaluminate or combination thereof. Given the novelty of the zincoaluminosilicate compositions described in this disclosure, it should be appreciated that in certain Aspects of this Embodiment, the zincoaluminosilicate or zincoaluminate is of a topology or composition different than the topology or composition of the intended product (e.g., different than the AEI, CHA, or GME topology eventually prepared and/or isolated, for example, as a FAU-zeolite source). In other Aspects of this Embodiment, the zincoaluminosilicate or zincoaluminate is the same topology or composition as the topology or composition of the intended product, for example, acting as seeds.

Embodiment 13. The process of any one of Embodiments 1 to 12, wherein the source of zinc oxide is or comprises a zinc(II) dicarboxylate, zinc(II) halide, zinc(II) hydroxide, zinc(II)oxide, zinc(II)nitrate, zincosilicate, zincoaluminate or zincoaluminosilicate. Given the novelty of the zincoaluminosilicate compositions described in this disclosure, it should be appreciated that in certain Aspects of this Embodiment, the zincosilicate, zincoaluminate or zincoaluminosilicate is of a topology or composition different than the topology or composition of the intended product (e.g., different than the AEI, CHA, or GME topology eventually prepared and/or isolated, for example, as a Zn—Al-containing FAU-zeolite source). In other Aspects of this Embodiment, the zincosilicate, zincoaluminate or zincoaluminosilicate is the same topology or composition as the topology or composition of the intended product, for example, acting as seeds.

Embodiment 14. The process of any one of Embodiments 1 to 12, wherein the source of silicon oxide is or comprises sodium silicate, the source of silicon and/or aluminum oxide is or comprises a FAU-zeolite, and the source of zinc oxide is or comprises zinc acetate. In related embodiments, the sources of silicon oxide, zinc oxide, and aluminum oxide is or comprises a Zn—Al-containing FAU molecular sieve.

Embodiment 15. The process of any one of Embodiments 1 to 13, wherein the mineralizing agent is or comprises an aqueous hydroxide. In certain Aspects of this Embodiment, the hydroxide is an alkali metal or alkaline earth metal hydroxide, for example including LiOH, NaOH, KOH, RbOH, CsOH, $Mg(OH)_2$, $Ca(OH)_2$, $Sr(OH)_2$, or $Ba(OH)_2$.

Embodiment 16. The process of any one of Embodiments 1 to 14, wherein the molar ratio of Al:Si is in a range of 0.005 to 0.2 (or the molar ratio of Si:Al is in a range of from 5 to 200). In certain specific Aspects of this Embodiment, the molar ratio of Al:Si is in a range of from 0.04 to 0.1.

Embodiment 17. The process of any one of Embodiments 1 to 15, wherein the molar ratio of OSDA:Si is in a range of 0.1 to 0.75. In certain specific Aspects of this Embodiment, the molar ratio of OSDA:Si is in a range of from 0.1 to 0.5.

Embodiment 18. The process of any one of Embodiments 1 to 16, wherein the molar ratio of water:Si is in a range of 5 to 50. In certain specific Aspects of this Embodiment, the molar ratio of water:Si is in a range of from 10 to 50 or from 10 to 25.

Embodiment 19. The process of any one of Embodiments 1 to 17, wherein the molar ratio of total hydroxide:Si is in a range of 0.1 to 1.25. In certain specific Aspects of this Embodiment, the molar ratio of total hydroxide:Si is in a range of from 0.4 to 1. As used herein, the term "total hydroxide" includes the amount of hydroxide introduced with the OSDA and separately.

Embodiment 20. The process of any one of Embodiments 1 to 18, wherein the molar ratio of Zn:Si is in a range of 0.01 to 0.2. In certain specific Aspects of this Embodiment, the molar ratio of Zn:Si is in a range of from 0.01 to 0.1

Embodiment 21. The process of any one of Embodiments 1 to 19, wherein the conditions effective to crystallize a crystalline microporous zincoaluminosilicate solid of AEI, CHA, or GME topology include treatment of the hydrothermally treated composition at a temperature in a range of from 100° C. to 200° C. for a time effective for crystallizing the crystalline microporous zincoaluminosilicate solid. In certain specific Aspects of this Embodiment, the temperature is in a range of from 120° C. to 180° C. In certain specific Aspects of this Embodiment, this time is in a range of from 1 hour to 14 days. In certain independent Aspects of this Embodiment, the times and temperatures include ranges described elsewhere herein.

Embodiment 22. The process of any one of Embodiments 1 to 20, further comprising isolating the crystalline microporous zincoaluminosilicate solid.

Embodiment 23. The process of Embodiment 21, further comprising heating the isolated crystalline microporous zincoaluminosilicate solid at a temperature in a range of from about 250° C. to about 600° C. to form an OSDA-depleted zincoaluminosilicate product. In certain specific Aspects of this Embodiment, where the product is a zincoaluminosilicate solid of GME topology, the temperature range is from about 250° C. to about 400° C. In certain independent Aspects of this Embodiment, the times and temperatures include ranges described elsewhere herein. In certain independent Aspects of this Embodiment, the heating is done in an oxidizing atmosphere, such as air or oxygen, or in the presence of other oxidizing agents. In other Aspects, the heating is done in an inert atmosphere, such as argon or nitrogen.

Embodiment 24. The process of Embodiment 21, further comprising contacting the isolated crystalline microporous zincoaluminosilicate solid with ozone or other oxidizing agent at a temperature in a range of 100° C. to 200° C. for a time sufficient to form an OSDA-depleted zincoaluminosilicate product. In certain specific Aspects of this Embodiment, the heating is done at a temperature of about 150° C. to form an OSDA-depleted product.

Embodiment 25. The process of Embodiment 21, wherein the isolated solid is a zincoaluminosilicate of GME topology, the process further comprising heating the isolated crystalline microporous zincoaluminosilicate solid at a temperature in a range of from about 200° C. to about 600° C. in the presence of an alkali, alkaline earth, transition metal, rare earth metal, ammonium or alkylammonium salts (anions including halide, preferable chloride, nitrate, sulfate, phosphate, carboxylate, or mixtures thereof) to form a dehydrated or an OSDA-depleted product. In certain Aspects of this Embodiment, the heating is done in the presence of NaCl or KCl. Aspects of this Embodiment, the heating is done at a temperature in a range of from 500 to 600° C. In still other Aspects of the Embodiment, the heating is done in either an oxidizing or inert atmosphere.

Embodiment 26. The process of any one of Embodiments 22 to 24, further comprising treating the dehydrated or OSDA-depleted product with an aqueous ammonium or metal cation salt. In some Aspects of this Embodiment, the salt is a halide salt. In some Aspects of this Embodiment, the metal salt comprises $K^+$, $Li^+$, $Rb^+$, $Cs^+$: $Co^{2+}$, $Ca^{2+}$, $Mg^{2+}$, $Sr^{2+}$; $Ba^{2+}$; $Ni^{2+}$; $Fe^{2+}$. In other specific Aspects, the metal cation salt is a copper salt or complex, for example, Schweizer's reagent (tetraamminediaquacopper dihydroxide, $[Cu(NH_3)_4(H_2O)_2](OH)_2]$), copper(II) nitrate, copper (II) carbonate or copper(II) acetate.

Embodiment 27. The process of any one of Embodiments 22 to 24, further comprising treating at least some pores of the calcined crystalline microporous zincoaluminosilicate solid with at least one type of transition metal or transition metal oxide. In certain Aspects of this Embodiment, the transition metal or transition metal oxide comprises a Group 4 to Group 12 metal. In certain independent Aspects of this Embodiment, the transition metal or transition metal oxide comprises an element of Groups 6, 7, 8, 9, 10, 11, or 12. In other independent Aspects of this Embodiment, the transition metal or transition metal oxide comprises Fe, Ru, OS, Co, Rh, Ir, Ni, Pd, Pt, Cu, Ag, or Au.

Embodiment 28. A composition prepared by any one of the processes of Embodiments 1 to 24.

Embodiment 29. A composition comprising:
(a) a source of a silicon oxide, and optionally a source of germanium oxide, or combination thereof;

(b) a source of aluminum oxide, and optionally a source of boron oxide, gallium oxide, hafnium oxide, iron oxide, tin oxide, titanium oxide, indium oxide, vanadium oxide, zirconium oxide, or combination or mixture thereof;

(c) a source zinc oxide;

(d) a mineralizing agent;

(e) an organic structure directing agent (OSDA) comprising at least one isomer of the quaternary piperidinium cation of Formula (I):

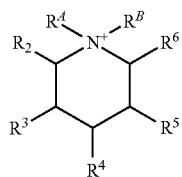
(I)

and (f) a compositionally consistent crystalline microporous zincoaluminosilicate solid of an AEI or GME topology;

wherein $R^A$ and $R^B$ are independently a $C_{1-3}$ alkyl, or together with the N to which they are bound form a 5 or 6 membered saturated or unsaturated ring; and $R^2$, $R^3$, $R^4$, $R^5$, and $R^6$ are independently H or $C_{1-3}$ alkyl, provided at least two of $R^2$, $R^3$, $R^4$, $R^5$, and $R^6$ are independently $C_{1-3}$ alkyl.

In some Aspects of this Embodiment, the OSDA comprises at least one isomer of the quaternary piperidinium cation of Formula (IA) or (IB):

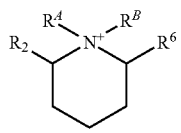
(IA)

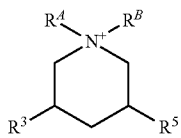
(IB)

wherein $R^2$ $R^3$, $R^5$, and $R^6$ are independently $C_{1-3}$ alkyl. In other Aspects of this Embodiment, the quaternary piperidinium cation has an associated bromide, chloride, fluoride, iodide, nitrate, or hydroxide anion. Each of these cations is an independent Aspect of this Embodiment. In other Aspects of this Embodiment, the composition is absent any source of aluminum oxide, boron oxide, gallium oxide, hafnium oxide, iron oxide, tin oxide, titanium oxide, indium oxide, vanadium oxide, or zirconium oxide.

Embodiment 30. The composition of Embodiment 29, wherein the quaternary piperidinium cation of Formula (I) is an N,N-dialkyl-2,6-lupetidinium cation or N,N-dialkyl-3,5-lupetidinium cation:

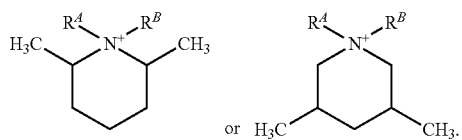

Embodiment 31. The composition of Embodiment 29 or 30, wherein the quaternary piperidinium cation of Formula (I) is cis-N,N-dialkyl-3,5-lupetidinium cation, trans-N,N-dialkyl-3,5-lupetidinium cation, cis-N,N-dialkyl-2,6-lupetidinium cation, trans-N,N-dialkyl-2,6-lupetidinium cation or a combination thereof:

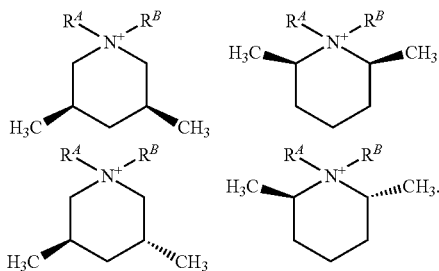

Each of these cations is an independent Aspect of this Embodiment.

Embodiment 32. The composition of Embodiment 30 or 31, wherein $R^{A,}$ and $R^B$ are both methyl.

Embodiment 33. A composition comprising:

(a) a source of a silicon oxide, and optionally a source of germanium oxide or combination thereof;

(b) a source of aluminum oxide, and optionally a source of boron oxide, gallium oxide, hafnium oxide, iron oxide, tin oxide, titanium oxide, indium oxide, vanadium oxide, zirconium oxide, or combination or mixture thereof; and (c) a source of a zinc oxide;

(d) a mineralizing agent;

(e) an organic structure directing agent (OSDA) comprising a trialkyladamantylammonium cation of Formula (II) or an optionally substituted trialkylbenzylammonium cation of Formula (III):

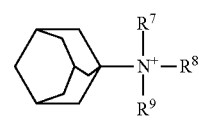
(II)

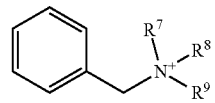
(III)

and (f) a compositionally consistent crystalline microporous zincoaluminosilicate solid of a CHA topology;

wherein:

$R^7$, $R^8$, and $R^9$ are independently $C_{1-6}$ alkyl or $C_{1-3}$ alkyl; and wherein the quaternary trialkyladamantyl- or trialkylbenzyl-ammonium cation has an associated bromide, chloride, fluoride, iodide, nitrate, or hydroxide anion. Each of the trialkyladamantylammonium cation of Formula (II) or an optionally substituted trialkylbenzylammonium cation of Formula (III) are considered independent Embodiments. In certain Aspects of this Embodiment, the phenyl group of the trialkylbenzylammonium cation may be optionally substituted with independently one to three fluoro or optionally fluorinated or perfluorinated $C_{1-3}$ alkyl groups.

Embodiment 34. The composition of Embodiment 33, wherein at least one of $R^7$, $R^8$, or $R^9$ is methyl or ethyl. In certain Aspects of this Embodiment, at least one of $R^7$, $R^8$, or $R^9$ is methyl. In other Aspects of this Embodiment, each one of $R^7$, $R^8$, or $R^9$ is methyl.

Embodiment 35. The composition of any one of Embodiments 29 to 34, wherein the quaternary cation has an associated fluoride or hydroxide ion preferably substantially free of other halide counterions. In separate Aspects of this Embodiment, the associated anion is hydroxide.

Embodiment 36. The composition of any one of Embodiments 29 to 35, comprising a source of silicon oxide, a source of aluminum oxide, and a source of zinc oxide. That is, the optionally sources of germanium oxide, boron oxide, gallium oxide, hafnium oxide, iron oxide, tin oxide, titanium oxide, indium oxide, vanadium oxide, or zirconium oxide are absent.

Embodiment 37. The composition of any one of Embodiments 29 to 36, wherein the source of aluminum oxide, boron oxide, gallium oxide, germanium oxide, hafnium oxide, iron oxide, tin oxide, titanium oxide, indium oxide, silicon oxide, vanadium oxide, zirconium oxide, or combination or mixture thereof is or comprises an alkoxide, hydroxide, oxide, or combination thereof of the corresponding metal.

Embodiment 38. The composition of any one of Embodiments 29 to 37, wherein the source of silicon oxide is or comprises an aluminosilicate, a zincoaluminosilicate, zincosilicate a silicate, silica hydrogel, silicic acid, fumed silica, colloidal silica, tetra-alkyl orthosilicate, a silica hydroxide, or combination thereof. Given the novelty of the zincoaluminosilicate compositions described in this disclosure, it should be appreciated that in certain Aspects of this Embodiment, the zincoaluminosilicate or zincosilicate is of a topology or composition different than the topology or composition of the intended product (e.g., different than the AEI, CHA, or GME topology eventually prepared and/or isolated). In other Aspects of this Embodiment, the zincoaluminosilicate or zincosilicate is the same topology or composition as the topology or composition of the intended product, for example, acting as seeds.

Embodiment 39. The composition of any one of Embodiments 29 to 38, wherein the source of aluminum oxide is or comprises an alkoxide, hydroxide, or oxide of aluminum, a sodium aluminate, an aluminum siloxide, an aluminosilicate, a zincoaluminosilicate, zincoaluminate, or combination thereof. Given the novelty of the zincoaluminosilicate compositions described in this disclosure, it should be appreciated that in certain Aspects of this Embodiment, the zincoaluminosilicate or zincoaluminate is of a topology or composition different than the topology or composition of the intended product (e.g., different than the AEI, CHA, or GME topology eventually prepared and/or isolated, for example, as a FAU-zeolite source). In other Aspects of this Embodiment, the zincoaluminosilicate or zincoaluminate is the same topology or composition as the topology or composition of the intended product, for example, acting as seeds.

Embodiment 40. The composition of any one of Embodiments 22 to 39, wherein the source of zinc oxide is or comprises a zinc(II) dicarboxylate, zinc(II) halide, zinc(II) hydroxide, zinc(II)oxide, zinc(II)nitrate, zincosilicate, zincoaluminate or zincoaluminosilicate. Given the novelty of the zincoaluminosilicate compositions described in this disclosure, it should be appreciated that in certain Aspects of this Embodiment, the zincosilicate, zincoaluminate or zincoaluminosilicate is of a topology or composition different than the topology or composition of the intended product (e.g., different than the AEI, CHA, or GME topology eventually prepared and/or isolated, for example, as a Zn—Al-containing FAU-zeolite source). In other Aspects of this Embodiment, the zincosilicate, zincoaluminate or zincoaluminosilicate is the same topology or composition as the topology or composition of the intended product, for example, acting as seeds.

Embodiment 41. The composition of any one of Embodiments 29 to 40, wherein the source of silicon oxide is or comprises sodium silicate, the source of Al is or comprises a FAU-zeolite, and the source of zinc oxide is or comprises zinc acetate. In related embodiments, the sources of both the zinc oxide and aluminum oxide is or comprises a Zn—Al-containing FAU molecular sieve.

Embodiment 42. The composition of any one of Embodiments 29 to 41, wherein the mineralizing agent is or comprises aqueous hydroxide. In certain Aspects of this Embodiment, the hydroxide is an alkali metal or alkaline earth metal hydroxide, for example including LiOH, NaOH, KOH, RbOH, CsOH, $Mg(OH)_2$, $Ca(OH)_2$, $Sr(OH)_2$, or $Ba(OH)_2$.

Embodiment 43. The composition of any one of Embodiments 29 to 42, wherein the molar ratio of Al:Si in the composition is in a range of from 0.005 to 0.2 (or the molar ratio of Si:Al is in a range of from 5 to 200). In certain specific Aspects of this Embodiment, the molar ratio of Al:Si is in a range of from 0.04 to 0.1.

Embodiment 44. The composition of any one of Embodiments 29 to 43, wherein the molar ratio of OSDA:Si in the composition is in a range of from 0.1 to 0.75. In certain specific Aspects of this Embodiment, the molar ratio of OSDA:Si is in a range of from 0.1 to 0.5.

Embodiment 45. The composition of any one of Embodiments 29 to 44, wherein the molar ratio of water:Si in the composition is in a range of from 5 to 50. In certain specific Aspects of this Embodiment, the molar ratio of water:Si is in a range of from 10 to 50 or from 10 to 25.

Embodiment 46. The composition of any one of Embodiments 29 to 45, wherein the molar ratio of total hydroxide:Si is in a range of from 0.1 to 1.25. In certain specific Aspects of this Embodiment, the molar ratio of total hydroxide:Si is in a range of from 0.4 to 1.

Embodiment 47. The composition of any one of Embodiments 29 to 46, wherein the molar ratio of Zn:Si in the composition is in a range of from 0.01 to 0.2. In certain specific Aspects of this Embodiment, the molar ratio of Zn:Si is in a range of from 0.01 to 0.1

Embodiment 48. The composition of any one of Embodiments 29 to 47, wherein the composition exists at a temperature in a range of from 100° C. to 200° C. In certain specific Aspects of this Embodiment, the temperature is in a range of from 120° C. to 180° C.

Embodiment 49. The composition of any one of Embodiments 29 to 48, that is a gel.

Embodiment 50. A crystalline microporous zincoaluminosilicate solid of GME or AEI topology having pores at least some of which are occluded with quaternary piperidinium cations of Formula (I):

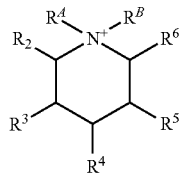
(I)

wherein $R^A$ and $R^B$ are independently a $C_{1-3}$ alkyl, or together with the N to which they are bound form a 5 or 6 membered saturated or unsaturated ring; and $R^2$, $R^3$, $R^4$, $R^5$, and $R^6$ are independently H or $C_{1-3}$ alkyl, provided at least two of $R^2$, $R^3$, $R^4$, $R^5$, and $R^6$ are independently $C_{1-3}$ alkyl.

In some Aspects of this Embodiment, the OSDA is or comprises at least one isomer of the quaternary piperidinium cation of Formula (IA) or (IB):

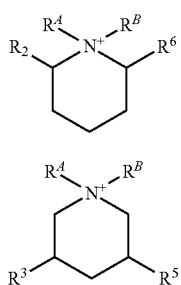
(IA)

(IB)

wherein $R^2$ $R^3$, $R^5$, and $R^6$ are independently $C_{1-3}$ alkyl. In other Aspects of this Embodiment, the quaternary piperidinium cation has an associated bromide, chloride, fluoride, iodide, nitrate, or hydroxide anion. In certain Aspects of this Embodiment, the composition is one characterized as a CIT-9 composition as described herein.

Embodiment 51. The crystalline microporous zincoaluminosilicate solid of Embodiment 50, wherein the quaternary piperidinium cation of Formula (I) is or comprises an N,N-dialkyl-2,6-lupetidinium cation or N,N-dialkyl-3,5-lupetidinium cation:

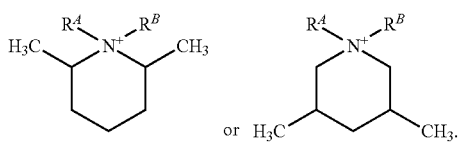

Embodiment 52. The crystalline microporous zincoaluminosilicate solid of Embodiment 49 or 50, wherein the quaternary piperidinium cation of Formula (I) is or comprises cis-N,N-dialkyl-3,5-lupetidinium cation, trans-N,N-dialkyl-3,5-lupetidinium cation, cis-N,N-dialkyl-2,6-lupetidinium cation, trans-N,N-dialkyl-2,6-lupetidinium cation or a combination thereof:

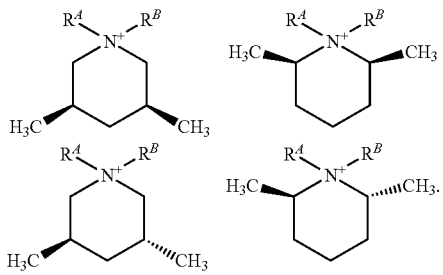

Embodiment 53. The crystalline microporous zincoaluminosilicate solid of Embodiment 51 or 52, wherein $R^{A'}$ and $R^B$ are both methyl.

In certain Aspects, the crystalline microporous zincoaluminosilicate solid of any one of Embodiments 50 to 53 (having a GME or AEI topology) having a molar ratio of Si:Al in a range of from 3 to about 20 (or $SiO_2/Al_2O_3$ ratio of from 6 to 40) and molar ratio of Si:Zn in a range from 5 to 30. Independent Aspects of this Embodiment includes those where the molar ratio of Si:Al in a range greater than 3.5 to about 15 (or $SiO_2/Al_2O_3$ ratio greater than 7 to about 30) or from 5 to 10 and a molar ratio of Si:Zn in a range from 8 to 26. Independent Aspects of this Embodiment include those ranges described elsewhere herein. In certain Aspects of this Embodiment, the crystalline microporous zincoaluminosilicate solid having a GME or AEI topology have these Si:Al and Si:Zn ratios when the pore are substantially depleted of OSDA.

Embodiment 54. A crystalline microporous zincoaluminosilicate solid of CHA topology having pores at least some of which are occluded with a trialkyladamantylammonium cation of Formula (II) or an optionally substituted trialkylbenzylammonium cation of Formula (III):

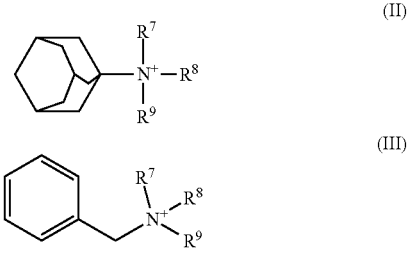
(II)

(III)

wherein:

$R^7$, $R^8$, and $R^9$ are independently $C_{1-6}$ alkyl or $C_{1-3}$ alkyl; and wherein the quaternary trialkyladamantyl- or trialkylbenzyl-ammonium cation has an associated bromide, chloride, fluoride, iodide, nitrate or hydroxide anion. The compositions containing the trialkyladamantylammonium cation of Formula (II) or an optionally substituted trialkylbenzylammonium cation of Formula (III) are considered independent Embodiments. In certain Aspects of this Embodiment, the phenyl group of the trialkylbenzylammonium cation may be optionally substituted with independently one to three fluoro or optionally fluorinated or perfluorinated $C_{1-3}$ alkyl groups.

Embodiment 55. The crystalline microporous zincoaluminosilicate solid of Embodiment 54, wherein at least one of $R^7$, $R^8$, or $R^9$ is methyl or ethyl. In certain Aspects of this Embodiment, at least one of $R^7$, $R^8$, or $R^9$ is methyl. In other Aspects of this Embodiment, each one of $R^7$, $R^8$, or $R^9$ is methyl.

In certain Aspects, the crystalline microporous zincoaluminosilicate solid of Embodiment 54 or 55 has a molar ratio of Si:Al in a range of from 4 to 100 (or $SiO_2/Al_2O_3$ ratio from 8 to 200) and a molar ratio of Si:Zn in a range from 10 to 50. Independent Aspects of this Embodiment include those where the molar ratio of Si:Al is in a range of from 4 to 12 or 6 to 10 and where the molar ratio of Si:Zn is in a range of from 18 to 36 or from 20 to 30 Independent Aspects of this Embodiment include those where these ratios are those ranges described elsewhere herein.

Embodiment 56. A crystalline microporous zincoaluminosilicate solid exhibiting at least one of the following:

(a) an X-ray diffraction (XRD) pattern the same as or consistent with any one of those shown in FIG. 3 (Zn—Al-AEI), FIG. 4 (Zn—Al-AEI), or FIG. 9 (Zn—Al-GME and Zn—Al-CHA);

(b) an XRD pattern having at least the five major peaks substantially as provided in Table 2.

(c) an $^{29}Si$ MAS spectrum for having a plurality of chemical shifts of about −110.5, −105, −99.5 ppm downfield of a peak corresponding to and external standard of tetramethylsilane (for Zn—Al-AEI); or (d) an $^{29}Si$ MAS spectrum the same as or consistent with the one shown in FIG. 8 for Zn—Al-AEI.

Additional Aspects of these Embodiments include those compositions of any one of Embodiments 50 to 53 which exhibit (e) a thermogravimetric analysis (TGA) curve the same as or consistent with the one shown in FIG. 5 (for Zn—Al-AEI) or (f); a thermogravimetric analysis (TGA) curve indicative of a loss of 8 to 20 wt %. In certain Aspects of this Embodiment, the pore are substantially depleted of OSDA.

Embodiment 57. A crystalline microporous zincoaluminosilicate solid having a GME or AEI topology. In some Aspects of this Embodiment, the zincoaluminosilicate solid having a GME or AEI topology has a molar ratio of Si:Al in a range of from 3 to 20 (or $SiO_2/Al_2O_3$ ratio of from 6 to 40) and molar ratio of Si:Zn in a range from 5 to 30. Independent Aspects of this Embodiment include those ranges described elsewhere herein. In certain Aspects of this Embodiment, the pore are substantially depleted of OSDA.

Embodiment 58. A crystalline microporous zincoaluminosilicate solid having a CHA topology. In some Aspects of this Embodiment, the zincoaluminosilicate solid having a CHA topology has a molar ratio of Si:Al in a range of from 4 to 100 (or $SiO_2/Al_2O_3$ ratio from 8 to 200) and molar ratio of Si:Zn in a range from 10 to 50. Independent Aspects of this Embodiment include those where the molar ratio of Si:Al is in a range of from 4 to 12 or 6 to 10 and where the molar ratio of Si:Zn is in a range of from 18 to 36 or from 20 to 30 Independent Aspects of this Embodiment include those where these ratios are those ranges described elsewhere herein. In certain Aspects of this Embodiment, the pore are substantially depleted of OSDA. In certain Aspects of this Embodiment, the crystalline microporous zincoaluminosilicate contains one or more of the OSDA described herein occluded within its pores. In other Aspects, the crystalline microporous zincoaluminosilicate is devoid or substantially devoid of such OSDAs.

Embodiment 59. The crystalline microporous zincoaluminosilicate solid of any one of Embodiments 56 to 58, comprising pores, at least some of which contain Li, Na, K, Rb, Cs, Be, Mg, Ca, Sr, Ba, Al, Ga, In, Zn, Ag, Cd, Ru, Rh, Pd, Pt, Au, Hg, La, Ce, Pr, Nd, Pm, Sm, Eu, or $R_{4-n}N^+H_n$ cations, where R is alkyl, n=0-4. In specific Aspects of this Embodiment, the pores contain NaCl or KCl.

Embodiment 60. The crystalline microporous zincoaluminosilicate solid of any one of Embodiments claims 56 to 59, comprising pores, at least some of which contain scandium, yttrium, tin, titanium, zirconium, vanadium, manganese, chromium, molybdenum, tungsten, iron, ruthenium, osmium, cobalt, rhodium, iridium, nickel, palladium, platinum, copper, silver, gold, or mixtures thereof, each as a metal, oxide, or salt. In one Aspect of this Embodiment, the pores contain copper, as metal, oxide, or salt.

Embodiment 61. A process comprising carbonylating DME with CO at low temperatures, reducing NOx with methane, reducing NOx with ammonia, converting methane via partial oxidation to methanol, converting methanol to at least one type of olefin, cracking, dehydrogenating, converting paraffins to aromatics, MTO, isomerizing xylenes, disproportionating toluene, alkylating aromatic hydrocarbons, oligomerizing alkenes, aminating lower alcohols, separating and sorbing lower alkanes, hydrocracking a hydrocarbon, dewaxing a hydrocarbon feedstock, isomerizing an olefin, producing a higher molecular weight hydrocarbon from lower molecular weight hydrocarbon, reforming a hydrocarbon, converting a lower alcohol or other oxygenated hydrocarbon to produce an olefin products, reducing the content of an oxide of nitrogen contained in a gas stream in the presence of oxygen, or separating nitrogen from a nitrogen-containing gas mixture by contacting the respective feedstock with a catalyst comprising the crystalline microporous zincoaluminosilicate solid of any one of claims 56 to 60 under conditions sufficient to affect the named transformation.

Embodiment 62. A process comprising reducing NOx in exhaust gases by catalytic reduction (e.g., with ammonia) or converting methane via partial oxidation to methanol, for examples with $O_2$, $H_2O_2$, or $N_2O$, with a catalyst comprising a copper changed crystalline microporous zincoaluminosilicate solid of Embodiment 60, under conditions sufficient to affect the named transformation. In certain Aspects of this Embodiment, the catalyst comprises a zincoaluminosilicate of AEI or CHA or GME topology, whose pores contain exchanged copper.

Embodiment 63. A process comprising contacting methanol with the crystalline microporous zincoaluminosilicate solid of Embodiment 58 to 60 (as applied to Embodiment 58) under conditions sufficient to convert the methanol to at least one type of olefin.

Embodiment 64. An ion exchange material comprising the zincoaluminosilicate of any one of claims 50 to 59.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees Celsius, pressure is at or near atmospheric.

Example 1. General Methods

Example 1.1. Materials and Methods cis-N,N-dimethyl-3,5-lupetidinium hydroxide (98/2 cis/trans) and trimethyladamantylammonium hydroxide was acquired from SACHEM Inc.

$^{29}Si$ NMR Bloch Decay (d1=60 s) spectra were measured on a Bruker 500 MHz spectrometer in a 4 mm $ZrO_2$ rotor at a spinning rate of 8 kHz and referenced externally versus tetramethylsilane. Additionally, a 200 MHz spectrometer was used with 7 mm rotors spinning at 4 kHz.

Thermogravimetric analysis (TGA) was performed on a Perkin Elmer STA 6000 with a ramp of 10° C. min$^{-1}$ to 900° C. under air atmosphere.

SEM was performed on a ZEISS 1550 VP FESEM, equipped with an Oxford X-Max SDD X-ray Energy Dispersive Spectrometer (EDS) system for determining the Si/Al, Cu/Al, Na/Al and Si/Zn ratios of the samples.

All Powder X-ray diffraction (PXRD) characterization was conducted on a Rigaku MiniFlex II with Cu K$_\alpha$ radiation.

Example 1.2. General Synthetic Methods

A general procedure for hydroxide syntheses was as follows. The OSDA in its hydroxide form was combined water in a 23 mL-Teflon Parr reactor. Then a silica source (N° Sodium silicate, PQ Corporation) and Zn$^{II}$-acetate.dihydrate (Sigma Aldrich) were added as well. Finally, the aluminum source (CBV500=NH$_4$-FAU of Zeolyst) was added. The synthesis was stirred until a homogenous gel was obtained. The Teflon Parr reactor was then sealed and placed in a rotating or static oven at 140° C. Aliquots of the synthesis gels were taken periodically as follows: quenching the reactor in water, opening the reactor, stirring its contents until homogeneous and finally, removing enough material for PXRD. After washing the aliquots once with water and once with acetone, they are left to dry in a 100° C. oven before PXRD measurement. The yields were calculated as follows (without compensation for the intermediate aliquots): the final dry weight obtained after thorough washing of the finished syntheses with water and acetone and drying at 100° C. is corrected with the weight loss of organic SDA and water in TGA up to 900° C. This corrected weight is assumed to be pure zincoaluminosilicate and is divided by the maximum theoretical possible zincoaluminosilicate formation from the input silica, alumina and zinc-oxide. The weight of inorganic cations present in the samples is hereby neglected. The reference aluminosilicate version of GME in FIG. 9 was made in conditions identical to those of entry 7 in Table 1, but with use of the classic Al source (NH$_4$-FAU) and thus without Zn addition.

The ozonolysis procedure for OSDA removal was carried out at 150° C. in a tube furnace by using a Longevity Resources ozone generator (setting at 2) and a oxygen gas flow of 200 cm$^3$/min over 100-500 mg of as-made zeolite sample. Cu ion-exchanges were performed overnight on calcined samples in concentrated Schweizer's reagent solutions at room temperature under continuous stirring and at loadings of 1 g·100 mL$^{-1}$. This was repeated 3 times. After exchange, the samples were calcined again.

General calcination was performed in dry flowing air by heating to 150° C. at 1° C./min; holding for 3 h at 150° C., and then heated further to 580° C. at 1° C./min and held for 6 h.

Example 2. Syntheses and Characterizations

Figure 2:
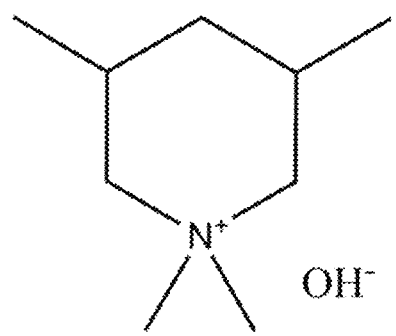
FIG. 2 shows the quaternized N,N-dimethyl-3,5-dimethylpiperidinium hydroxide OSDA.

Table 1 shows conditions for the preparation of a range of zincoaluminosilicate compositions. A zincoaluminosilicate with the AEI topology, hereafter denoted Zn—Al-AEI, was made using a quaternized N,N-dimethyl-3,5-dimethylpiperidine organic structure directing agent (OSDA) in combination with a Si source, Al-source, Zn-source, water and (sodium) hydroxide as a mineralizing agent. The OSDA is structurally illustrated in FIG. 2. Representative reaction conditions which have been used to prepare Zn—Al-AEI are shown in Table 1, Entries 1-4, along with a control synthesis of a pure aluminosilicate AEI (SSZ-39), in entry 5. A CHA and GME recipe is found in entries 6 and 7, as discussed elsewhere herein.

TABLE 1

Typical Zn-Al-AEI syntheses reactions with N,N-dimethyl-3,5-dimethylpiperidinium hydroxide (98 cis/2% trans) as the OSDA (unless noted otherwise), NH4-FAU (CBV500, Si/Al 2.6) as aluminum source, sodium silicate as silicon source and Zn-acetate for providing Zn; unless otherwise noted.

| no | Gel composition relative to Si[1] (molar ratios based on Si = 1) | | | | | time (days) | phase | Si/Al | Si/Zn | Yield (%) | sample name |
|---|---|---|---|---|---|---|---|---|---|---|---|
| | Al | Zn | OSDA | H$_2$O | OH$^-$ | | | | | | |
| 1 | 0.067 | 0.033 | 0.17 | 20.0 | 0.67 | 9 | AEI | 8.4 | 10.7 | n.d. | MDU78 |
| 2 | 0.067 | 0.033 | 0.17 | 20.0 | 0.67 | 14 | AEI | 7.6 | 11.1 | 48 | MDU147 |
| 3[2] | 0.066 | 0.032 | 0.17 | 20.0 | 0.67 | 14 | AEI | 7.7 | 11.3 | 56 | MDU143 |
| 4[3] | 0.067 | 0.033 | 0.17 | 20.0 | 0.67 | 21 | AEI* | n.d. | n.d. | 49 | MDU223 |
| 5[4] | 0.033 | / | 0.14 | 20.7 | 0.71 | 3 | AEI[5] | 7.6 | / | 26 | MDU182 |
| 6[6] | 0.067 | 0.033 | 0.17 | 20.1 | 0.67 | 7 | CHA | 8.4 | 26.2 | 31 | MDU148 |
| 7[7] | 0.055 | 0.017 | 0.18 | 20.3 | 0.72 | 4 | GME | 3.6 | 23.1 | 10 | MDU215 |

[1]Synthesis at 140° C. in a rotating oven. OH− is the sum of inorganic and OSDA derived hydroxide contents. The inorganic derived hydroxide is calculated from the presence of NaOH, which is calculated from the total Na content, originating from NaOH addition and sodium silicate. The Zn source is Zn(II) acetate. dihydrate. The total OH− content is not corrected for neutralization deriving from the acetate addition. n.d. = not determined.
[2] Repeat of entry 2, but at 2.5x the scale.
[3]Repeat of entry 2, but syntheses at 5x the scale in a static oven.
[4]OSDA is N,N-dimethyl-2,6-dimethylpiperidinium hydroxide instead.
[5]Note that the phase is also AEI, but the material is a pure aluminosilicate, called SSZ-39, see reference (2).
[6]OSDA is trimethyladamantylammonium hydroxide instead.

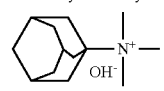

trimethyladamantylammonium hydroxide

[7]Instead of adding Zn-acetate in the gel, a different home-made FAU zeolite containing Zn, Si and Al was used as source for both Zn and Al (and partially Si). This Na-FAU was made along the recipe provided in Hunsicker, R. A.; Klier, K.; Gaffney, T. S.; Kirner, J. G. Chem. Mater. 2002, 14, 4807 and Chen, J.; Thomas, J. M. *J. Chem. Soc., Chem. Commun.* 1994, 603.and had Si/Al 3.2 and Si/Zn 10.2.
*Presence of a small impurity, probably GME noted.

The syntheses in Table 1 (Entries 1 to 4) demonstrated that the method is reproducible and that larger scale and static reactions are possible. The materials were obtained in modest yields (based on the maximum theoretical silica, alumina and zinc-oxide formation) and with Si/Al ratios of about 8 and Si/Zn ratios around 11. The SSZ-39 from entry 5 had a similar Si/Al of 7.6.

One evidence of the synthesis of a new, Zn and Al containing siliceous AEI material can be found in the synthesis times. While normal SSZ-39 synthesis in similar conditions lasts only three days; the synthesis conditions with Zn in the gel crystallized much more slowly. This could be an indication of either a Zn-acetate induced, slower formation of regular SSZ-39 or the formation of a new Zn—Al-AEI material. In the case of the former, Zn could be present in the solid sample as ZnO, causing a bulk Si/Zn measure in EDS. To further corroborate that the latter was happening, viz. the formation of a new AEI material with both Zn and Al in a siliceous framework, extensive characterization and additional arguments were gathered and shown as follows.

Example 2.1. Characterizations by Powder X-Ray Diffraction (PXRD)

Based on a comparison of the PXRD patterns obtained as a result of these syntheses (FIG. 3) with patterns provided in the literature (see, e.g., IZA-Structure-Commission, *Database of Zeolite Structures*, http://izasc.biw.kuleuven.be/fmi/xsl/IZA-SC/ft.xsl, Accessed 23 Jan. 2015; U.S. Pat. No. 5,958,370 (to Zones, et al.); and Wagner, P., et al., *J. Am. Chem. Soc.* 1999, 122, 263) it was clear that all zinc-containing phases produced in entries 1-4 of Table 1 possessed the AEI framework topology. See Table 2. The clean SSZ-39 (AEI) from MDU182 (entry 5) presented a good comparison, as did the pattern of pure zinc-oxide. Reflections of the latter were clearly not found in any of the Zn—Al-AEI samples and ruled out the formation of PXRD-visible ZnO next to SSZ-39 in the Zn—Al-AEI syntheses.

TABLE 2

PXRD data for representative zincoaluminosilicates.
Values in 2θ. See also FIG. 3, FIG. 4, and FIG. 9.

| Zn—Al-AEI | Zn—Al-GME | Zn—Al-CHA |
|---|---|---|
| 9.4 ± 0.2 | 7.4 ± 0.2 | 9.5 ± 0.2 |
| 10.5 ± 0.2 | 11.5 ± 0.2 | 14.0 ± 0.2 |
| 13.9 ± 0.2 | 14.9 ± 0.2 | 16.1 ± 0.2 |
| 16.1 ± 0.2 | 17.8 ± 0.2 | 17.7 ± 0.2 |
| 16.8 ± 0.2 | 19.8 ± 0.2 | 20.8 ± 0.2 |
| 17.1 ± 0.2 | 21.7 ± 0.2 | 24.9 ± 0.2 |
| 20.7 ± 0.2 | 27.8 ± 0.2 | 26.1 ± 0.2 |
| 21.3 ± 0.2 | 30.1 ± 0.2 | 30.8 ± 0.2 |
| 23.9 ± 0.2 | | |

Further manipulation of the MDU143 sample was performed and the resulting PXRD analyses are found in FIG. 4. The treatments involved calcination under air at 580° C., ozone-treatment at 150° C., TGA analysis with ramping at 10° C.·min$^{-1}$ under air and a Cu$^{2+}$ exchange (viz. below). The material maintained most of its crystallinity in all cases, except in the TGA ramping procedure, where the sample was brought to 900° C. The PXRD pattern of that treatment is indicative of a structural collapse and will be further discussed.

Example 2.2. Characterizations by Thermal Gravimetric Analysis (TGA)

The TGA analyses of an as-made Zn—Al-AEI is shown in FIG. 5, along with a calcined and ozone-treated version. The weight loss in the region of 300-900° C. (with a distinct profile) in the case of the as-made material was attributed to the loss of the OSDA incorporated in the structure from synthesis. The thermal weight profile of the calcined and ozone-treated samples clearly showed that both methods efficiently removed the organic (and that water takes up some of the available space).

Figure 6:
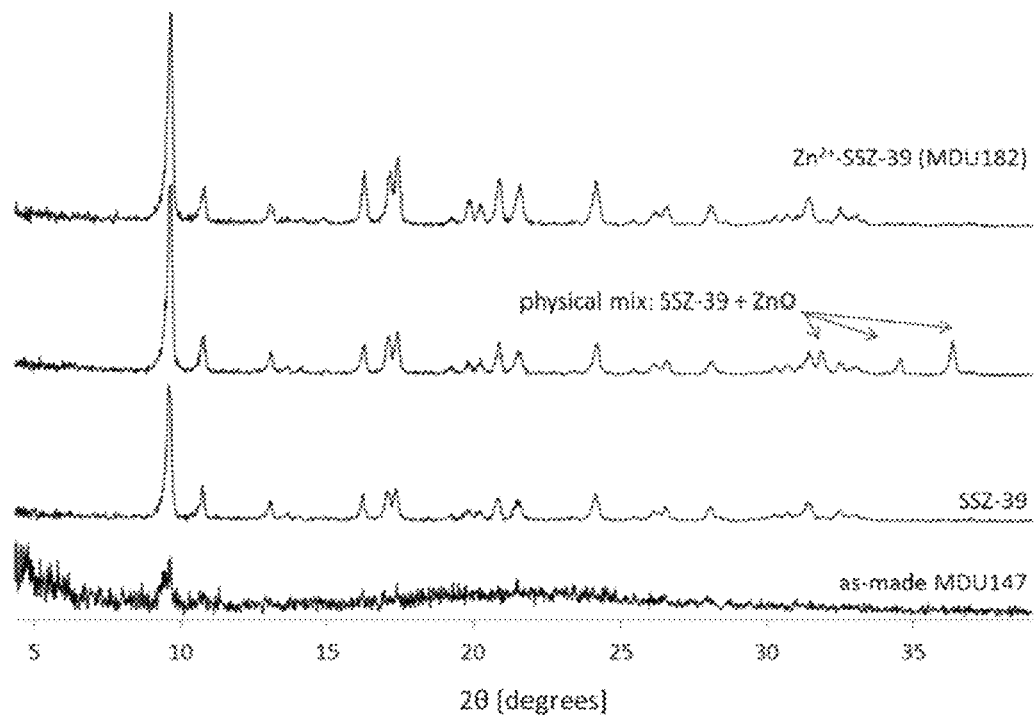
FIG. 6 shows PXRD on samples after TGA analyses up to 900° C. of MDU147 and three control SSZ-39-based samples.

Beside weight loss information, the TGA analysis provided a reliable way to assess the stability of materials. TGA can be a harsh thermal treatment that can destroy microporous materials due to the high temperatures reached (900° C.), as well as the fast ramping rate (10° C./min). As FIG. 4 already indicated, the as-made Zn—Al-AEI lost a great deal of its PXRD reflections and thus partially collapsed in TGA. This was never seen for various control SSZ-39 samples, where all reflections remained with good intensities in PXRD following TGA. As straightforward comparison can be seen in FIG. 6 along with two additional controls: a Zn$^{2+}$-exchanged SSZ-39 (with a measured Zn/Al ratio of 0.3, obtained via Zn-nitrate exchange of a calcined MDU182) and a physical mixture of as-made SSZ-39 and ZnO (15 wt %). In both controls, the PXRD visible crystallinity was totally preserved after TGA, indicative of the fact that the collapse of the Zn—Al-AEI material was not the collapse of a physical mixture of SSZ-39 induced by the presence of extra-framework Zn species. In other words, if the Zn—Al-AEI was either a physical mixture of SSZ-39 ("aluminosilicate Al-AEI") and ZnO or a Zn-exchanged SSZ-39, the structural collapse could not be explained. The collapse in TGA was also observed for the calcined and ozone-treated Zn—Al-AEI materials (not shown).

Example 2.3. Characterizations by Ion-Exchange Balance

Once having prepared these materials, there was an expectation that the ion-exchange capacity (and especially for divalent cations such as Cu$^{2+}$) would be higher for these zincoaluminosilicate matrices relative to the aluminosilicate analogs, especially given that both samples have a similar Al content (Si/Al ratio). A complication with zinc species in tetrahedral framework positions was the relative ease of their hydrolysis and subsequent leaching in even slightly acidic media. It was noted that traditional ion-exchange methods affected the Si/Zn ratios (e.g. when 1M NH$_4^+$-nitrate solutions were used, the Si/Zn ratio rose from 11.3 to 39.3 for calcined MDU143). Because of the increasing insolubility of Cu$^{2+}$ species at pH>6.5, a Schweizer's reagent (tetraaminediaquacopper dihydroxide) was used as ion-exchange medium. This provided a slightly basic way (pH around 9) to introduce Cu$^{2+}$ to the exchange sites and so protect the Zn sites from hydrolysis. By calcination, the ammonium ligands were then removed and the Si/Zn, Si/Al, and Cu/Al ratios were measured by EDS (Table 3) for an exchanged SSZ-39 and Zn—Al-AEI. A remarkable difference was found between SSZ-39 and Zn—Al-AEI: the latter could exchange 0.35 Cu/Al (mol/mol), while the former could only attain a 0.24 Cu/Al ratio. Even though some Zn seemed to be lost in the exchange (Si/Zn rose from 11 to 15), a 45% larger ion-exchange capacity was thus found for the new material, strongly indicative that at least a significant part of the Zn atoms are present in the tetrahedral (alumino) siliceous AEI framework. Moreover, the high Na/Al ratio of the washed, calcined MDU143 material (Table 3) supported this conclusion: a high 1.8 value was obtained, whereas for classic SSZ-39 samples (not measured for MDU182), Na/Al values below 0.5 are usually obtained. In this case, along with the OSDA cation, Na$^+$ compensated part of the framework charge during synthesis.

TABLE 3

Composition of MDU182 and MDU143 after calcination, ion-exchange via Schweizers reagent, and another calcination, compared to before exchange.

| synthesis | type of material* | | before exchange | | | after exchange | |
|---|---|---|---|---|---|---|---|
| | | Na/Al | Si/Al | Si/Zn | Cu/Al | Si/Al | Si/Zn |
| MDU182 | Na$^+$-SSZ-39 (Al-AEI) | n.d. | 8.0 | / | 0.24 | 7.5 | / |
| MDU143 | Na$^+$—Zn—Al-AEI | 1.8 | 7.3 | 11.3 | 0.35 | 6.7 | 15.5 |

*From synthesis, all framework negative charges that are not balanced by OSDA are compensated by Na$^+$ due to the high Na content of the gels.

Example 2.4. Characterizations by $^{29}$Si-NMR

Figure 7:
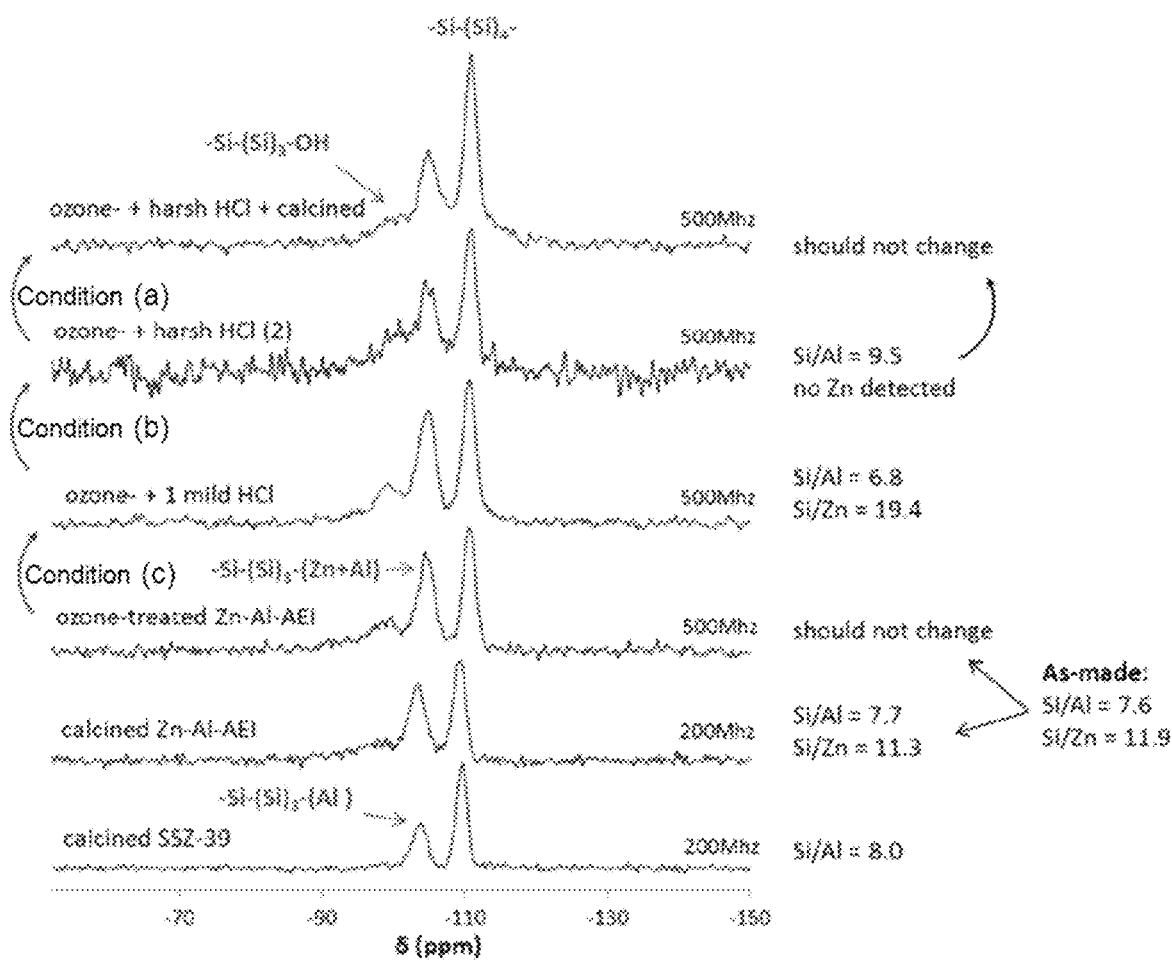
FIG. 7 shows full overview of $^{29}$Si MAS (Bloch Decay) NMR for a series of treatments on Zn—Al-AEI (MDU143) compared to the calcined SSZ-39 sample (MDU182). Both 500 and 200 MHz spectrometers used, as indicated. This is the origin of the slight contraction of the main two signals (for instance visible when comparing calcined and ozone-treated Zn—Al-AEI). In the figure, Condition (a) is calcination at 580° C.; Condition (b) is treatment in 0.3 M HCl overnight at 60° C.; Condition (c) is treating with 0.01 M HCl, 4 hours at room temperature

The final and most direct proof for the present characterization was the observation of additional Zn-derived signals in the $^{29}$Si NMR spectra of the Zn—Al-AEI materials when compared to the Zn-free SSZ-39 (FIG. 7). Both materials had a similar Si/Al ratio (viz. Table 1, 2). The ratio of the signal of Si—(Si)$_4$— sites at –110 ppm and the Si—(Si)$_3$—(Al) sites at –105 ppm of about 2:1 in SSZ-39 was in line with its Si/Al ratio of about 8 of and the presence of mainly isolated Al sites in the siliceous matrix. The calcined and ozone-treated Zn—Al-AEI materials displayed a much higher signal at –105 ppm. This was likely due to the superposition of both Si—(Si)$_3$—(Zn) and Si—(Si)$_3$—(Al) signals. The Si/Al ratio of this material (7.7) could not have caused the –105 ppm signal to be nearly as intense as the –110 ppm signal. Additionally, in these new materials, a signal at –98 ppm was found, that was likely related to the presence of silanols [Si—(Si)$_3$—(OH)] in the material. This could for instance be enhanced by the presence of trifold tethered Zn in a siliceous environment, when one of the tetrahedral Zn—O—Si bond has been hydrolyzed or did not form completely. Considering the ease of hydrolysis demonstrated in the exchange experiments, this was likely. To further support the present conclusion that the additional signals in the Zn—Al-AEI derived from framework Zn, the ozone-treated Zn—Al AEI material was acid-treated, first in mild and then in harsh conditions (for conditions, see FIG. 7). The mild treatment did not remove much of the Zn from the framework as evidenced by the Si/Zn ratio of 19 mentioned next to the NMR trace and the trace itself. After the harsh treatment, no Zn could be detected with EDS. And after calcination, the $^{29}$Si NMR spectra of the harsh treated one resembled that of the calcined aluminosilicate SSZ-39. The crucial overlays of this Zn-free Zn—Al-AEI with both the SSZ-39 and the Zn—Al-AEI are shown in FIG. 8. The PXRD trace of this material was also identical to that of a calcined SSZ-39 (not shown) and its reflections were stable after TGA analysis (not shown), confirming the removal of Zn and the creation of a type of SSZ-39 from a Zn—Al-AEI by removing the framework Zn. This confirms the presence of framework zinc in the starting material.

Example 2.4. Extension to Other Frameworks

The synthesis and properties of a novel zincoaluminosilicate having AEI topology is crystalline and isostructural with AlPO-18 and SSZ-39, as it has a framework with the AEI topology (framework code of the structure commission of the International Zeolite Association). To further extend the methodology, the synthesis of zincoaluminosilicates with the GME and CHA topologies are also shown.

Entries 6 and 7 of Table 1 demonstrate the relative ease with which the synthesis of Zn—Al-CHA and Zn—Al-GME was possible using similar synthetic recipes with the right OSDA and adequate conditions. The corresponding PXRD traces of these materials can be found in FIG. 9 and match well with databases. For GME, an aluminosilicate control is given, with a Si/Al ratio of 4.1. Some of the reflections of the Zn—Al-GME were clearly shifted towards lower 2θ values (viz. dashed lines). This indicated that there was a measurable enhancement in certain dimensions of the unit cell for the zincoaluminosilicate version of GME, a framework with 12MR 1-dimensional channels. This was expected given the larger nature of Zn atoms and the higher level of heteroatom (Al+Zn) substitution in the zincoaluminosilicate framework.

Example 3. Final Comments

Figure 1B:
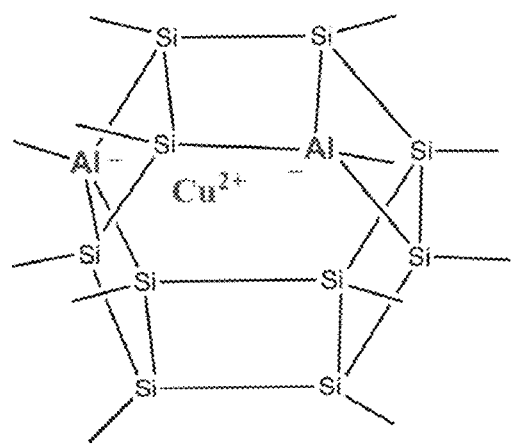
Figure 1C:
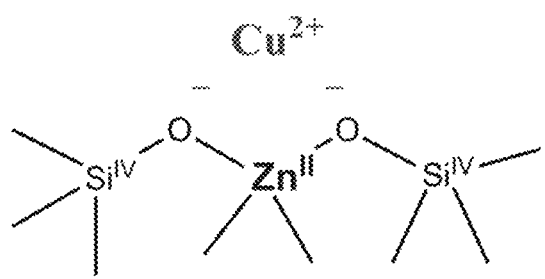

The totality of the available data support the conclusion that at least part of the Zn atoms in the Zn—Al-AEI material are present as tetrahedral framework species in an aluminosilicate matrix. Based on the AEI, CHA and GME examples, it is also shown that this zincoaluminosilicate synthesis method can be extended to other framework types, especially for those topologies where aluminosilicate compositions with high Al content are easily formed and more specifically, for topologies that contain the d6r composite building block (see International Zeolite Association, Database of Zeolite Structures), seen in FIG. 1(B)). These two criteria are common denominators for CHA, AEI and GME type materials.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

All of the references cited in this disclosure are incorporated by reference herein in their entireties for all purposes.

What is claimed:

1. A crystalline microporous zincoaluminosilicate solid having a GME topology, having a molar ratio of Si:Al in a range of from 3 to 200 and molar ratio of Si:Zn in a range from 5 to 50.

2. The crystalline microporous zincoaluminosilicate solid of claim 1, exhibiting at least one of the following:
   a) an XRD pattern the same as or consistent with a pattern shown in FIG. 9 associated with the crystalline microporous zincoaluminosilicate solid having a GME topology; or b) an XRD pattern having at least five of the peaks having 2-theta values at 7.4±0.2°, 11.5±0.2°, 14.9±0.2°, 17.8±0.2°, 19.8±0.2°, 21.7±0.2°, 27.8±0.2°, or 30.1±0.2°.

3. The crystalline microporous zincoaluminosilicate solid of claim 1, that exhibits an XRD pattern the same as or consistent with a pattern shown in FIG. 9 associated with the crystalline microporous zincoaluminosilicate solid having a GME topology.

4. The crystalline microporous zincoaluminosilicate solid of claim 1, that exhibits an XRD pattern having at least five of the peaks having 2-theta values at 7.4±0.2°, 11.5±0.2°, 14.9±0.2°, 17.8±0.2°, 19.8±0.2°, 21.7±0.2°, 27.8±0.2°, or 30.1±0.2°.

5. The crystalline microporous zincoaluminosilicate solid of claim 1, the crystalline microporous zincoaluminosilicate solid of GME topology having pores that contain an organic structure directing agent (OSDA) comprising quaternary piperidinium cations of Formula (I):

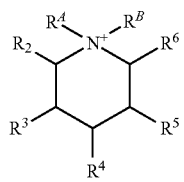

wherein $R^A$ and $R^B$ are independently a $C_{1-3}$ alkyl, or together with the N to which they are bound form a 5 or 6 membered saturated or unsaturated ring; and $R^2$, $R^3$, $R^4$, $R^5$, and $R^6$ are independently H or $C_{1-3}$ alkyl, provided at least two of $R^2$, $R^3$, $R^4$, $R^5$, and $R^6$ are independently $C_{1-3}$ alkyl.

6. The crystalline microporous zincoalummosilicate solid of claim 5, wherein the OSDA comprises at least one isomer of the quaternary piperidinium cation of Formula (IA) or (IB):

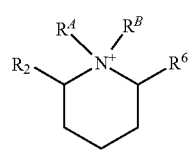

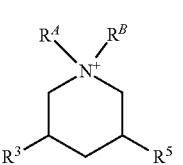

wherein $R^2$, $R^3$, $R^5$, and $R^6$ are independently $C_{1-3}$ alkyl.

7. The crystalline microporous zincoaluminosilicate solid of claim 5, wherein the OSDA comprises an N,N-dialkyl-2,6-lupetidinium cation or N,N-dialkyl-3,5-lupetidinium cation:

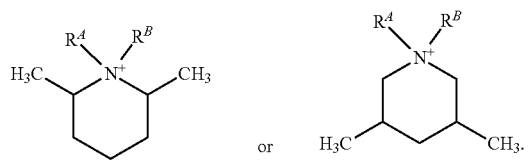

8. The crystalline microporous zincoalummosilicate solid of claim 5, wherein the quaternary piperidinium cation of Formula (I) comprises a cis-N,N-dimethyl-3,5-lupetidinium cation, trans-N,N-dimethyl-3,5-lupetidinium cation, cis-N,N-dimethyl-2,6-lupetidinium cation, trans-N,N-dimethyl-2,6-lupetidinium cation or a combination thereof.

9. The crystalline microporous zincoaluminosilicate solid of claim 1 whose micropores are substantially free of organic structure directing agent.

10. The crystalline microporous zincoaluminosilicate solid of claim 1, comprising pores that optionally contain:
(a) Li, Na, K, Rb, Cs, Be, Mg, Ca, Sr, Ba, Al, Ga, In, Zn, Ag, Cd, Ru, Rh, Pd, Pt, Au, Hg, La, Ce, Pr, Nd, Pm, Sm, Eu, or $R_{4-n}N^+H_n$ cations, where R is alkyl, n=0-4; or
(b) scandium, yttrium, titanium, tin, zirconium, vanadium, manganese, chromium, molybdenum, tungsten, iron, ruthenium, osmium, cobalt, rhodium, iridium, nickel, palladium, platinum, copper, silver, gold, or mixtures thereof, each as a metal, oxide, or salt.

11. The crystalline microporous zincoalummosilicate solid of claim 1, comprising pores in their hydrogen form.

12. The crystalline microporous zincoaluminosilicate solid of claim 1, comprising pores that contain Li, Na, K, Rb, Cs, Be, Mg, Ca, Sr, Ba, Al, Ga, In, Zn, Ag, Cd, Ru, Rh, Pd, Pt, Au, Hg, La, Ce, Pr, Nd, Pm, Sm, Eu, or $R_{4-n}N^+H_n$ cations, where R is alkyl, n=0-4.

13. The crystalline microporous zincoaluminosilicate solid of claim 1, comprising pores that contain scandium, yttrium, titanium, tin, zirconium, vanadium, manganese, chromium, molybdenum, tungsten, iron, ruthenium, osmium, cobalt, rhodium, iridium, nickel, palladium, platinum, copper, silver, gold, or mixtures thereof, each as a metal, oxide, or salt.

14. A process for preparing a zincoaluminosilicate composition of claim 1, the process comprising hydrothermally treating an aqueous composition comprising:
(a) a source of a silicon oxide, and optionally a source of germanium oxide or combination thereof;
(b) a source of aluminum oxide, and optionally a source of boron oxide, gallium oxide, hafnium oxide, iron oxide, tin oxide, titanium oxide, indium oxide, vanadium oxide, zirconium oxide, or combination or mixture thereof; and
(c) a source of a zinc oxide;
(d) a mineralizing agent; and
(e) an organic structure directing agent (OSDA) comprising at least one isomer of the quaternary piperidinium cation of Formula (I):

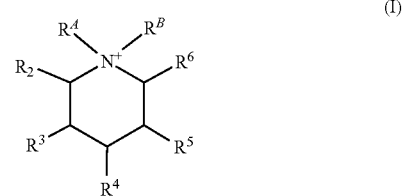

under conditions to crystallize a crystalline microporous zincoaluminosilicate solid of GME topology; wherein
$R^A$ and $R^B$ are independently a $C_{1-3}$ alkyl, or together with the N to which they are bound form a 5 or 6 membered saturated or unsaturated ring; and
$R^2, R^3, R^4, R^5$, and $R^6$ are independently H or $C_{1-3}$ alkyl, provided at least two of $R^2, R^3, R^4, R^5$, and $R^6$ are independently $C_{1-3}$ alkyl; wherein
the quaternary piperidinium cation has an associated bromide, chloride, fluoride, iodide, nitrate, or hydroxide anion.

15. The process of claim 14, wherein the OSDA comprises at least one isomer of the quaternary piperidinium cation of Formula (IA) or (IB):

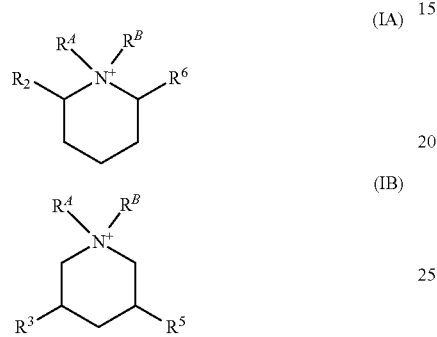

wherein $R^2 R^3$, $R^5$, and $R^6$ are independently $C_{1-3}$ alkyl.

16. The process of claim 14, wherein the quaternary piperidinium cation of Formula (I) comprises an N,N-dialkyl-2,6-lupetidinium cation or an N,N-dialkyl-3,5-lupetidinium cation:

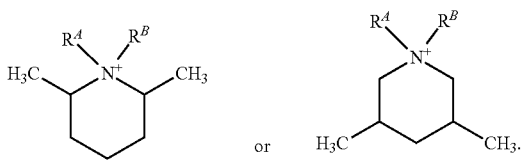

17. The process of claim 14, wherein the quaternary piperidinium cation of Formula (I) comprises cis-N,N-dimethyl-3,5-lupetidinium cation, trans-N,N-dimethyl-3,5-lupetidinium cation, cis-N,N-dimethyl-2,6-lupetidinium cation, trans-N,N-dimethyl-2,6-lupetidinium cation or a combination thereof:

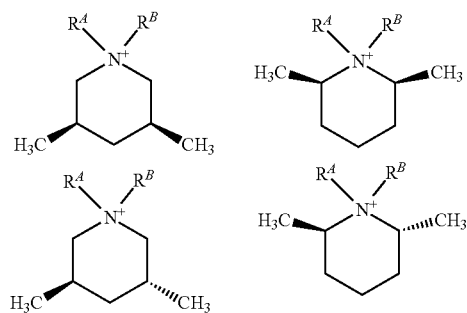

and the associated anion is hydroxide.

18. The process of claim 14, wherein:
(a) the source of silicon oxide is or comprises an aluminosilicate, a zincoaluminosilicate, a zincosilicate, a silicate, silica hydrogel, silicic acid, fumed silica, colloidal silica, tetra-alkyl orthosilicate, a silica hydroxide or combination thereof;
(b) the source of aluminum oxide is or comprises an alkoxide, hydroxide, or oxide of aluminum, a sodium aluminate, an aluminum siloxide, an aluminosilicate, a zincoaluminosilicate, zincoaluminate or combination thereof;
(c) the source of zinc oxide is or comprises a zinc(II) dicarboxylate, zinc(II) halide, zinc(II) hydroxide, zinc (II)oxide, zinc(II)nitrate, zincosilicate, zincoaluminate or zincoaluminosilicate.

19. The process of claim 14, wherein the source of silicon oxide comprises sodium silicate, the source of Al comprises a FAU-zeolite, and the source of zinc oxide comprises zinc acetate.

20. The process of claim 14, wherein the mineralizing agent comprises an aqueous alkali metal or alkaline earth metal hydroxide.

21. The process of claim 14, wherein:
(a) the molar ratio of Al:Si is in a range of 0.005 to 0.2;
(b) the molar ratio of OSDA:Si is in a range of 0.1 to 0.75;
(c) the molar ratio of water:Si is in a range of 5 to 50;
(d) the molar ratio of total hydroxide:Si is in a range of 0.1 to 1.25; and
(e) the molar ratio of Zn:Si is in a range of 0.01 to 0.2.

22. The process of claim 14, wherein the conditions to crystallize a crystalline microporous zincoaluminosilicate solid of GME topology include treatment of the hydrothermally treated composition at a temperature in a range of from 100° C. to 200° C.

23. The process of claim 14, further comprising isolating the crystalline microporous zincoaluminosilicate solid.

24. The process of claim 23, further comprising the steps of:
(a) heating the isolated crystalline microporous zincoaluminosilicate solid at a temperature in a range of from 250° C. to 600° C.; or
(b) contacting the isolated crystalline microporous zincoaluminosilicate solid with ozone or other oxidizing agent at a temperature in a range of 100° C. to 200° C.; or
(c) heating the isolated crystalline microporous zincoalummosilicate solid at a temperature in a range of from 200° C. to 600° C. in the presence of an alkali, alkaline earth, transition metal, rare earth metal, ammonium or alkylammonium salt;
to form a dehydrated or an OSDA-depleted product.

25. The process of claim 24, further comprising treating the dehydrated or OSDA-depleted product with an aqueous ammonium or alkali, alkaline earth metal, transition, or rare earth metal cation salt.

26. The process of claim 25, further comprising treating the calcined crystalline microporous zincoaluminosilicate solid with at least one transition metal or transition metal oxide.

27. An ion exchange material comprising a crystalline microporous zincoaluminosilicate solid of claim 1.

* * * * *